United States Patent

Dursch et al.

[11] 4,096,208
[45] Jun. 20, 1978

[54] POLYPHOSPHINITES AND A PROCESS FOR THEIR PREPARATION

[75] Inventors: Walter Dursch; Fritz Linke, both of Konigstein, Taunus; Manfred Finke, Fischbach, Taunus, all of Germany

[73] Assignee: Hoechst Aktiengesellschaft, Frankfurt am Main, Germany

[21] Appl. No.: 749,792

[22] Filed: Dec. 13, 1976

[30] Foreign Application Priority Data

Dec. 16, 1975 Germany .............................. 2556482
Oct. 9, 1976 Germany .............................. 2645786
Oct. 22, 1976 Germany .............................. 2647745

[51] Int. Cl.² .............................................. C07F 9/32
[52] U.S. Cl. .................................. 260/931; 260/455 P; 260/502.4 R; 260/502.4 P; 260/932; 427/390 D
[58] Field of Search .................................. 260/931, 971

[56] References Cited

U.S. PATENT DOCUMENTS 3,900,506    8/1975    Bell et al. .......................... 260/931 X Primary Examiner—Anton H. Sutto
Attorney, Agent, or Firm—Connolly and Hutz

[57] ABSTRACT

Compounds of the formula

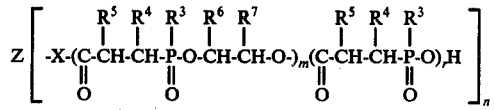

wherein Z is alkyl with 2 to 6 carbon atoms, x is oxygen, NH or sulfur, n and m are integers from 2 to 6, r is zero or 1, $R^4$, $R^5$ $R^6$ and $R^7$ are hydrogen or methyl and $R^3$ is methyl, ethyl or phenyl. They are obtained by reacting 1 mole of a compound of formula

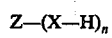

with $n.m$ moles of an alkyleneoxide or alkylenecarbonate of the formulas

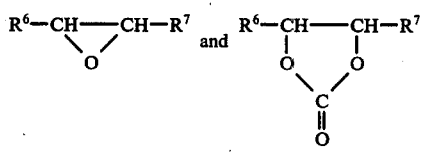

and $n(m+r)$ moles of a phospholane of formula

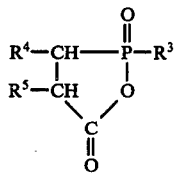

These compounds are used as flameproofing agents especially for pile carpets.

4 Claims, No Drawings

POLYPHOSPHINITES AND A PROCESS FOR THEIR PREPARATION

The present invention relates to a process for the preparation of polyaddition products containing phosphorus.

In contrast to polycondensation processes, polyaddition reactions do not form any waste products which need to be separated and, if necessary, be destroyed or — in the case of recycling — be purified.

Thus, it is possible in a particularly easy manner to introduce homogeneous atom groupings into basis molecules by way of polyaddition reactions. In this way, for example, polyethers carrying hydroxyl terminal groups having specific properties can be prepared in a single very easy reaction step by polyaddition of alkylene oxides to compounds with active hydrogen atoms.

The synthesis of easily accessible polyaddition products having recurrent atom groups containing phosphorus, especially phosphinic acid ester groups, has not been known so far. However, easily accessible substances having a high phosphorus content are of particular interest due to the valuable specific properties of phosphorus functions.

The addition of 2,5-di-oxo-1,2-oxa-phospholanes to monovalent alcohols and monovalent amines with the formation of phosphinic acids has already been described. The addition of 1,2-alkylene oxides to dialkyl-phosphinic acids is also already known. In these cases, compounds having only one phosphorus atom per molecule are obtained.

The present invention provides compounds having the general formula

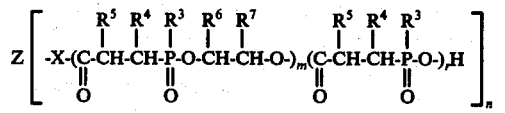

in which

X stands for identical or different radicals selected from the group of O, S and/or $NR^1$ with $R^1$ being hydrogen or $(C_1-C_4)$-alkyl, preferably hydrogen or methyl, $R^3$ is a $(C_1-C_4)$-alkyl group which may be substituted, preferably monosubstituted, by halogen, especially chlorine, a cycloalkyl group having up to 8 carbon atoms, especially cyclopentyl, cyclohexyl, an alkenyl group having up to 4 carbon atoms, especially vinyl and allyl, a phenyl or benzyl group optionally substituted by halogen, preferably chlorine and/or bromine, and preferably carrying 1 to 3 substituents, $R^4$ is hydrogen or a $(C_1-C_4)$-alkyl group, preferably methyl, $R^5$ is hydrogen or a $(C_1-C_2)$-alkyl group, preferably methyl, with at least one of the radicals $R^4$ and $R^5$ preferably being hydrogen, $R^6$ is hydrogen, methyl, chloromethyl, $R^7$ is hydrogen, methyl or ethyl, preferably hydrogen, m stands for numbers in the range of from 1 to 20, preferably from 2 to 20, especially from 2 to 6, n stands for numbers in the range of from 1 to 6, preferably from 2 to 6, r is 0 or 1, preferably 0, Z is a n-valent radical of the group consisting of: straight-chain or branched hydrocarbon radicals having from 1 to 18, preferably from 1 to 12, carbon atoms which may be interrupted by up to 8 -O-atoms, generally up to (q/2-1) —O-atoms, if q is the number of carbon atoms in Z, and/or by up to 3 —S-atoms and/or $NR^2$ radicals with $R^2$ being $(C_1-C_4)$-alkyl, especially methyl, and/or may be substituted by fluorine, chlorine, bromine atoms, preferably Cl and Br, while carrying preferably substituents in a number of up to half the H-atoms contained in Z, especially from 1 to 4; cyclohexyl radicals which may be substituted by from 1 to 3, preferably one straight-chain or branched and/or unsaturated alkyl radical having from 1 to 4 carbon atoms, or by a $(C_1-C_4)$-alkyl radical carrying preferably up to 4 F, Cl, or Br-atoms, aromatic or araliphatic radicals which are derived from benzene, alkyl benzenes having up to 18 carbon atoms, from naphthalene, diphenyl, diphenylmethane, diphenylethane, or 2,2-diphenylpropane, and which may be substituted in the nucleus by 1 or 2 methoxy and/or ethoxy groups, and which may be substituted in the nucleus and/or the lateral chains by F, Cl or Br-atoms, preferably carrying up to 5 substituents, or phosphate-containing radicals of the general formula

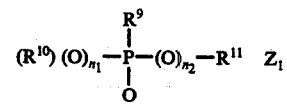

in which $n_1$, $n_2$ are independently from each other 0 and 1 and $R^9$ stands for alkyl, hydroxyalkyl, optionally $(C_1-C_2)$-alkylated and/or -dialkylated aminoalkyl, halogeno-(preferably chloro-)alkyl having 1 to 3 carbon atoms, alkenyl having 2 or 3 carbon atoms or phenyl optionally substituted by 1 or 2 halogen atoms, preferably Cl, or Br, $R^{10}$, $R^{11}$ may be defined as $R^9$ - if the pertinent $n_1$ and/or $n_2$ equals 0 — with the restriction that for $n_1 = n_2 = 0$ at least one of the radicals $R^{10}$, $R^{11}$ is an $(C_1-C_3)$— alkylene radical or, if the pertinent $n_1$ and/or $n_2$ equals 1, is a straight-chain or branched alkylene radical having from 2 to 5 carbon atoms or is the radical

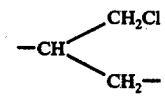

or represent phosphorus-containing radicals of the general formula

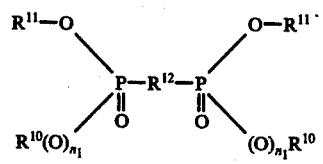

with $n_1$, $R^{16}$, $R^{11}$ being defined as in $Z_1$ and $R_{12}$ being a straight-chain or branched $(C_1-C_6)$-alkylene, phenylene, xylylene radical or a radical

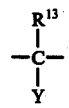

with Y = OH, NH$_2$ and R$^{13}$ = (C$_1$–C$_3$)-alkyl, or phosphorus-containing radicals of the general formula

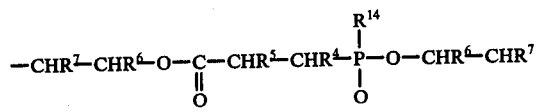

in which R$^4$, R$^5$, R$^6$, R$^7$ are defined as in formula I above and R$^{14}$ is defined as R$^3$ or represents the group —O—CHR$^6$—CHR$^7$—.

Preference is given in particular to compounds of the formula I in which Z is alkyl having 2 to 6 carbon atoms, X is oxygen, n and m are numbers of from 2 to 6, r is 0 and R$^4$ to R$^7$ is hydrogen or methyl and R$^3$ is methyl, ethyl or phenyl.

The invention further provides mixtures of compounds of the formula I.

Moreover, the invention provides a process for the preparation of the compounds of formula I, which comprises mixing a compound of the formula

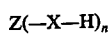 (II)

(a$_1$) with the about n times molar amount of a phospholane of the formula

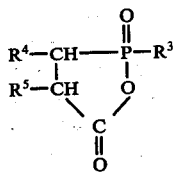 III heating it at a temperature of from 0° to 180° C, preferably 80° to 150° C, to give a phosphinic acid of the formula

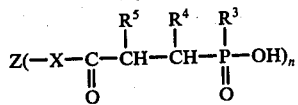 IIa$_1$ and, when this reaction has been completed, which can be seen from the disappearing of the phospholane peak at 5 500 mμ, (a$_2$) reacting the product thus obtained with the about n times molar amount of an alkylene oxide of the formula

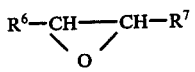 IV or of an alkylene carbonate of the formula

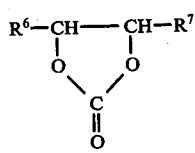 V to give a phosphinic acid-(hydroxyalkyl)-ester of the formula

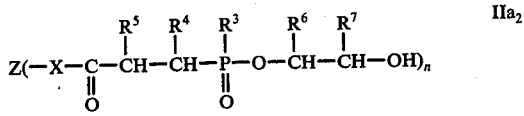 IIa$_2$ and, when this reaction has been completed, which can be seen from the acid number being 0, repeating the operation a$_1$ (m−1+r) times and following every operation a$_1$ repeating operation a$_2$ — (m−1) times altogether — or, preferably, (b) mixing a compound of the formula II with the n.m times molar amount of an alkylene oxide of the formula IV or of an alkylene carbonate of the formula V and with the about n(m+r) times molar amount of a phospholane of the formula III at a temperature of from 10° to 180° C, preferably 20° to 120° C, and maintaining the mixture after the reaction heat has disappeared, preferably while stirring, at the reaction temperature indicated below, until the reaction has been completed, which can be seen from the disappearing of the phospholane peak or of the carbon dioxide development and/or for r = 0, also of the acid number.

In formulae II through V the symbols are defined as in formula I.

The reaction of the phosphinic acids of the formula IIa with the alkylene oxides of the formula IV is carried out at a temperature of from 80° to 180° C, preferably from 100° to 150° C. If alkylene carbonates of the formula V are used, the reaction temperature is in the range of from 130° to 250° C, preferably from 160° to 220° C.

The process of the invention is generally carried out by introducing the compound of the formula III and adding compound II at a temperature exceeding its melting point, preferably at reaction temperature. The process may also be effected vice versa, however. After the reaction heat has cooled off, the alkylene oxide IV is added in the gaseous or liquid phase, depending on its boiling point. In order to prevent losses of volatile substances, it is advantageous to work while using a reflux condenser and/or to carry out the process in a closed vessel under autogenous pressure, which is essentially determined by the steam pressure of the alkylene oxides. However, the alkylene oxides may also be used in any desired excess amount, preferably in an amount exceeding the necessary quantity 1.2 to 2 times, and the alkylene oxide escaping the reaction mixture may be recovered in known manner, for example by condensation. The reaction with alkylene carbonates of the formula V may be effected in a way that the compounds of formulae V and III are introduced at room temperature and compound II is slowly added at a temperature above solution temperature. However, if compound II is not an amine, it may be introduced simultaneously. The reaction temperatures developing in the reaction of compounds II and III remain harmless in the presence of the alkylene carbonates V.

By adding basic catalysts in an amount of from 0.05 to 4.0%, preferably 0.2 to 2.0%, calculated on the sum of the compounds III and IV used, which are selected preferably from the group of alkali metal hydroxides, such as NaOH, KOH, alkali metal-(C$_1$–C$_4$)-alcoholates, such as Na-methylate, K-tert.-butylate, alkali metal-(bi)-carbonates, such as sodium carbonate, potassium carbonate, Na-, K-bicarbonate, the reaction rates are markedly increased. Depending on the reaction temperature, the reaction time is generally in the range of from about 1 to 120 hours, preferably from 1 to 20 hours. Naturally, it becomes longer with the increase of m, in particular for $m>4$, than for a lower m.

Naturally, it is also possible to produce basis compounds of formula II in situ by reacting alkylene oxides and/or alkylene carbonates with free carboxylic, phosphinic or phosphonic acids and to further react the same according to the invention. In this case, an additional s-molar amount of alkylene oxides or alkylene carbonates would be required, if s is the number of the free acid groups.

This formation of the compounds of the invention having recurrent atom groupings, starting from a bivalent alcohol, such as glycol (with $-X-$ being $-O-$, $Z = C_2H_4$ and n being 2) as basis compound and using, for example, alkylene carbonate, may be described by the following scheme:

(generally $m+r$) are always formed, if one more mole of III ($r=1$) rather than of IV and/or V (generally $m+1$ moles III) is used.

Neutral 2-hydroxyalkylesters 1, 2, 3, 4 etc. are formed, if the number of the reacted molecules IV and/or V is at least equal to the number of the molecules of II, i.e. if it is also at least equal to m ($r = O$). Analogous formulations are obtained, if instead of a bivalent alcohol, for example glycol ($n = 2$) n-valent alcohols of the general formula $Z(-OH)_n$ are used as starting products, with Z having the general meaning indicated above. In case there are not present alcohols as basis molecules, but for example any amines or mercapto compounds, the "acids 1, 2, 3, 4 etc." and "esters 1, 2, 3, 4 etc." being formed differ from those formulated with glycol as a basis in that the groups $Z(-X-)_n$ are to be introduced into the formula scheme instead of the groups $CH_2CH_2(-O-)_2$, with $-X-$ corresponding to the bridges $-S-$ or $-NR^1-$.

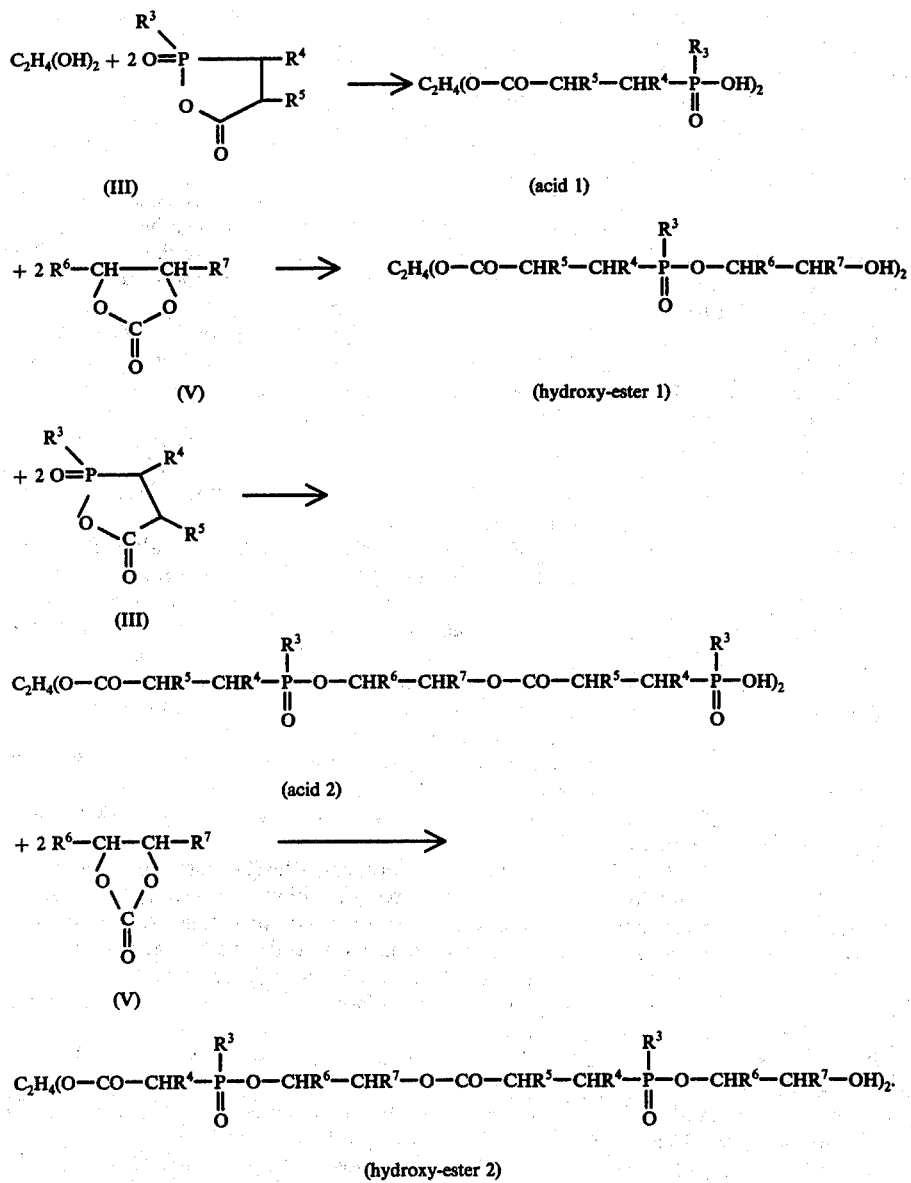

With further molecules of III and IV and/or V, the chain can still grow. When m is the number of molecules V used per growing chain, acids 1, 2, 3, 4 etc.

bridges $-S-$ or $-NR^1-$.

As starting products there may be used compounds of the formula II, in which X is the same (for example, polyalcohols, polyphenols, polyamides) or different (aminoalcohols, aminophenols, mercaptophenols), and also mixtures of compounds of formula II may be used as starting compounds in order to obtain mixtures of compounds of formula I. However, it is also possible to use mixtures of compounds of formula III and/or V as starting products, thus obtaining the corresponding mixtures of formula I or mixed added compounds of formula I. It is also possible to use for the oxalkylation reactions the compounds V, i.e. alkylene carbonates, as well as the compounds IV, i.e. alkylene oxides, at the same time. In this manner the positive solution properties of the alkylene carbonates may be connected with the more favorable price of the alkylene oxides.

In correspondence with the general reactivity of basis compounds having active hydrogen atoms (formula II) with phospholanes of the formula III and subsequently with alkyl carbonates of the formula V, in which process finally a compound of formula II is again obtained, there may be mentioned very extensive classes of compounds as basis substances for the process of the invention, which comprise a large part of organic chemistry. Although the possibilities of reaction are far more varied, the invention is to be limited for formal reasons to the basic classes of compounds II $Z(-XH)_n$ generally defined above.

As basic classes of compounds II that can be obtained most easily there are preferred hydroxyl compounds, if —X— represents an —O— bridge. Of the monovalent organic hydroxyl compounds with n = 1 there are mentioned, for example, all easily accessible aliphatic straight-chain and branched alcohols having from 1 to about 18 carbon atoms. The most important are, for example, methanol, ethanol, n-propanol, i-propanol, n-butanol, sec.-butanol, n-hexanol, 2-ethyl-butanol-1, n-octanol, 2-ethyl-hexanol-1, n-dodecanol, n-hexadecanol, n-octadecanol, the alcohols having from 1 to 4 carbon atoms being preferred. Polyhydric alcohols with n = 2–6 are even more favorable than monofunctional alcohols.

Of the polyvalent aliphatic polyols with n = 2–6 there are mentioned, for example: ethylene-glycol, 1,2-propylene-glycol, 1,3-propylene-glycol, 1,4-butane-diol, neopentyl-glycol, 1,6-hexane-diol, glycerol, trishydroxy-methylethane, trishydroxy-methylpropane, pentaerythritol, sorbitol, mannitol. Preference is given particularly to glycerol, pentaerythritol and sorbitol.

Of unsaturated alcohols there may be mentioned, for example, n-butene-2-ol-1, 1,4-butene-diol and allyl alcohol, with 1,4-butene-diol being preferred as bivalent alcohol.

Of the numerous compounds in which in an aliphatic hydrocarbon radical one or several —CH$_2$— groups are replaced by ether bridges —O—, there are suitable, for example, the reaction products of monovalent alcohols with one or several molecules of alkylene oxides or alkylene carbonates, such as, for example: 2-Methoxy-ethanol, 2-ethoxy-ethanol, 2-n-butoxy-ethanol, 2-(2'-ethyl-hexyloxy)-ethanol, 2-n-dodecyloxy-ethanol, moreover, the reaction products of 1 mole of methanol, 1 mole of ethanol or 1 mole of isopropanol and 2 moles of ethylene oxide or alkylene carbonate, i.e. methyl-diglycol, ethyl-diglycol and/or isopropyl-diglycol, furthermore, the reaction products of 3 to 7 molecules of ethylene oxide or ethylene carbonate with 1 mole of methanol, ethanol, isobutanol.

Appropriate reaction products of ethylene oxide and bivalent alcohols are, for example, the so-called diglycol and triglycol and the high-molecular weight reaction products of ethylene oxide and/or ethylene carbonate with water or ethylene-glycol having up to 18 carbon atoms, the so-called polyethylene-glycols having various molecular weights up to a medium molecular weight of 400, especially diglycol and triglycol, and there are suitable, furthermore, for example the addition products of 1 to 6 molecules of ethylene oxide and/or ethylene carbonate with tri- or polyhydric alcohols (n = 3–6), such as glycerol, trishydroxy-methyl-propane, pentaerythritol, etc.

Besides reaction products of ethylene oxide and/or ethylene carbonate with mono- or polyhydric alcohols there may also be mentioned reaction products of mono- and polyhydric alcohols with other 1,2-alkylene oxides and/or 1,2-alkylene carbonates, such as in particular, 1,2-propylene oxide, 1,2-propylene carbonate or epichlorhydrin, as well as the reaction products of ethylene oxide and/or ethylene carbonate with poly-1,2-propylene-glycols which are prepared as surface-active compounds in a wide variation, as has already been known. There are mentioned in particular corresponding poly-1,2-propylene-glycols and corresponding addition products of ethylene oxide and/or ethylene carbonate to (poly)-1,2-propylene oxides.

Besides by —O— bridges, the hydrocarbon chain of aliphatic hydroxyl compounds may also be interrupted by other hetero atoms, for example, by the elements N, S and/or P or carboxylic acid ester groups. These compounds may be obtained in a particularly easy manner, for example, by reacting one or several molecules of 1,2-alkylene oxides and/or 1,2-alkylene carbonates with ammonia, primary or secondary amines, hydrogen sulfide, mercaptans and with oxo-acids of phosphorus, ($C_2$–$C_6$)-carboxylic acids and/or dicarboxylic acids.

Of these reaction products with 1,2-alkylene oxides and/or 1,2-alkylene carbonates, there may be mentioned, for example:

With N in the molecule: the tertiary alkanolamines, such as tri-ethanolamine, methyl-diethanolamine, n-butyl-diethanol-amine, tetra-hydroxyethyl-ethylenediamine, pentahydroxyethyl-diethylene-triamine, n-dodecyl-diethanolamine, dimethyl-ethanol-amine, n-butyl-methyl-ethanolamine, di-n-butyl-ethanolamine, n-dodecyl-methyl-ethanolamine and the corresponding high-molecular-weight reaction products of these tertiary amines with ethylene oxide and/or ethylene carbonate or propylene oxide and/or propylene carbonate having a total number of carbon atoms of up to 18 per molecule.

With S in the molecule: Bis-(2-hydroxyethyl)-sulfide, bis-(2-hydroxy-propyl)-sulfide, bis-(2-hydroxyethyl)-sulfone and their reaction products with a further amount of ethylene oxide and/or ethylene carbonate or propylene oxide and/or propylene carbonate having a total number of carbon atoms of up to 18 C-atoms per molecule.

With P in the molecule: Neutral reaction products of 1,2-ethylene oxides, such as ethylene oxide, propylene oxide, epichlorhydrin, especially ethylene oxide and-/or, for example, ethylene carbonate with mono- and polyvalent alkane-phosphonic acids having from 1 to 18 carbon atoms, for example, with n-butane-, isobutane-, 2-ethyl-hexane-, n-octane-, decane-, dodecane-, tetradecane-phosphonic acid, especially with methane-, ethane-, propane- and vinyl-phosphonic acid and 1,2- ethane-diphosphonic acid, furthermore, with mono- or polyvalent di-alkyl-phosphinic acids, such as methyl-butyl-phosphinic acid, methylene-n-octyl-phosphinic acid, methyl-n-dodecyl-phosphinic acid and in particular dimethyl-, ethyl-methyl-, methyl-propyl-, methyl-vinyl-phosphinic acid and ethane-1,2-bis-(methyl-phosphinic acid), and additionally reaction products of 1 to 2 moles of alkylene oxide and/or ethylene carbonate with monovalent aliphatic carboxylic acids, such as crotonic acid, especially acetic acid, propionic acid, butyric acid and polyvalent aliphatic carboxylic acids, such as succinic acid and adipic acid.

The reaction of the various phosphorus-containing acids and of carboxylic acid in particular with alkylene oxides and/or alkylene carbonates may also be effected in the presence of the phosphorus compounds III. In the course of this process, intermediate products containing hydroxyl groups are formed in the reaction mixture, the former products acting as basis compounds II $Z(-XH)_n$ and reacting with the compounds III present in an excess amount and with further molecules IV to give the final products. Therefore, it is also possible to use carboxylic acids or — for example — phosphorus-containing free acids without additional —XH-groups directly as starting compounds. This method often simplifies the process considerably.

Thus, there are to be mentioned as possible starting compounds yielding the basis compounds II in situ for this process in particular the free carboxylic, phosphonic and phosphinic acids for example, which may contain hydroxyalkyl groups and which may also include, besides a free acid group, one or several OH groups, such as, for example, glycolic acid, 2-hydroxy-propionic acid, lactic acid, 2-hydroxyethyl-phosphonic acid, hydroxymethyl-phosphonic acid, 2-hydroxyethyl-methyl-phosphinic acid, etc. However, it is also possible to obtain further compounds of the formula II by using anhydrides of phosphonic, phosphinic, carboxylic acids or dicarboxylic acids as starting products, by reacting the same with compounds of the formula II and subsequently oxalkylating them with compounds of the formulae IV and V.

In the total balance, one more molecule of the 1,2-alkylene oxides IV and/or 1,2-alkylene carbonates V is needed altogether per free acid group or acid group to be set free.

Besides these hydroxyl compounds which may very easily be obtained by oxalkylation reactions and which include the hetero-atoms N, S and P, numerous further compounds with hydroxyalkyl groups and, optionally, with said heteroatoms and/or carboxylic acid ester groups in the hydrocarbon chain are also appropriate, such as, for example, oligo-condensation products being formed by the reaction of dicarboxylic acids or dicarboxylic acid anhydrides with polyhydric alcohols, moreover, glycolic acid-methylester, 2-hydroxyethane-carboxylic acid-ethylester, etc.

There are also suitable, for example, hydroxymethane-phosphonic acid-dimethylester, 2-hydroxyethane-phosphonic acid-diethylester, 3-hydroxypropane-phosphonic acid-di-n-butylester, etc. and analogous compounds of the phosphinic acid series, such as hydroxymethyl-methyl-phosphinic acid-methylester, 2-hydroxyethyl-methyl-phosphinic acid-ethylester, 3-hydroxypropyl-methyl-phosphinic acid-2'-ethyl-hexylester, hydroxymethyl-dimethyl-phosphine oxide, 2-hydroxyethyl-dimethyl-phosphine oxide.

All the analogous aliphatic hydroxyl compounds mentioned above or not mentioned before may be substituted by the halogen atoms chlorine, bromine, fluorine, especially by chlorine and bromine. There are to be mentioned, for example, the easily accessible compounds indicated in the following, which are interesting due to their favorable flameproof properties: 2-Bromoethanol, 2,3-dibromopropanol-1,2,3-dibromo-butanediol-1,4, dibromo-succinc acid-bis-(2-hydroxyethyl)-ester, 2-dibromopropane-phosphonic acid-bis-(2-hydroxyethyl)-ester, 2-hydroxyethane-phosphonic acid-bis-(2,3-dibromopropyl)-ester, moreover, chloroethanol, 2,3-dichloro-propanol-1, 1,3-dichloro-propanol-2,2,3-dichloro-butanediol-1,4, 2-hydroxyethane-phosphonic acid-bis(2,3-dichloropropyl)-ester, 1-chloro-vinyl-phosphonic acid-bis( 2-hydroxyethyl)-ester.

The compounds having reactive groups, in which one or several —X— are identical with a —NHR$_1$-bridge, include monovalent aliphatic primary and/or secondary amines whose hydrocarbon radicals may be interrupted by oxygen, carboxylic acid ester groups or by sulfur or phosphorus functions and may be substituted by hydroxyl groups, such as, for example, methylamine, ethylamine, isopropylamine, n-butylamine, 2-ethyl-hexylamine, dodecylamine, octadecylamine etc., ethylamine, diethylenetriamine, 1,4-butylene-diamine, etc., dimethylamine, diethylamine, di-n-butylamine, methyl-n-dodecylamine, methyl-n-octadecylamine, di-n-dodecylamine, etc., N,N'-dimethyl-ethylenediamine, furthermore, ethanolamine, isopropylamine, n-octyl-2-hydroxy-propylamine, n-tetra-2-hydroxy-ethylamine, N,N'-bis(2-hydroxyethyl)-ethylene-diamine, mono-2-hydroxy-propyl-diethylene triamine, etc., also the reaction products of mono- or polyvalent glycidyl compounds with ammonia or primary amines, for example, n-butyl-3-amino-2-hydroxy-1,2-bis-(3-methylamino-2-hydroxypropyl)-ether etc., for example, so-called diamino-polyethyleneglycols, i.e. polyethylene-glycols of a different molecular weight of up to about 600, in which the terminal hydroxy groups have been replaced by —NH$_2$, and for example the bis-(3-amino-2-hydroxypropyl)-ethers of polyethylene-glycols having a different molecular weight of up to about 500.

Of esters with amino groups there are mentioned the esters of 2-amino-carboxylic acid, of protein units, such as aminoacetic acid-methylester, α-aminopropionic acid-ethylester, α-ε-diaminocaproic acid-isopropylester, etc. It is also possible to use free amino acids in the reaction mixture because of the conversion of the free carboxyl groups into hydroxyl intermediate products.

As amine having a phosphorus function there may be used, for example, 3-amino-propyl-dimethyl-phosphine oxide which may easily be obtained from allylamine and dimethyl-phosphine oxide.

Of compounds in which —X— represents the bridge —S— there may be mentioned, for example, hydrogen sulfide and aliphatic compounds having mercapto groups, such as methyl-, ethyl-, n-butyl-, n-octyl-, n-dodecyl-mercaptan, β-mercapto-ethanol, thioglycolic acid-ethylester and also, for example, thioglycolic acid, since the carboxyl group is primarily converted into the 2-hydroxy-alkylester.

Of the derivatives of cyclohexane, which are substituted by n -XH-radicals, there are to be mentioned, above all:

Cyclohexanol, methylcyclohexanol, 1,4-dihydroxy-cyclohexane, 1,3-dihydroxy-cyclohexane, 1,4-diamino-cyclohexane.

There is also a large selection of appropriate aromatic compounds carrying n —XH-radicals. If —XH— stands for —OH, there may be mentioned all the so-called phenols in the broader sense, such as, for example, phenol, pyrocatechol, resorcinol, hydroquinone, pyrogallol, oxyhydroquinone, phloroglucinol, the various tetra- and pentahydroxy-benzenes, hexaoxybenzene, α-naphthol, β-naphthol, moreover, hydroxynaphthalenes having more than one hydroxy group, such as, for example, 1,2-, 1,3-, 1,4-, 1,5-, 1,6-, 1,7-, 1,8-, 2,3-dihydroxy-naphthalenes, moreover, 4-hydroxydiphenyl, 4,4'-dihydroxy-diphenyl, and — due to its favorable price — especially 2,2-bis-(4-hydroxyphenyl)-propane and 4,4'-bis-(4-hydroxy-phenyl)-methane. Also partially etherified polyvalent aromatic hydroxyl compounds, such as hydroquinonemonomethylether, resorcinol-monoethylether, etc. are appropriate.

Owing to their favorable influence of the flameproof properties, aromatic chloro- and especially bromo-hydroxy-compounds are of particular interest, such as, for example, 2,4,6-tribromo-phenol, pentabromo-phenol, 2,4,6trichlorophenol or pentachloro-phenol and 2,2-bis-(4-hydroxy-3,5-dibromo-phenyl)-propane.

Moreover, there are suitable aromatic hydroxyl compounds having alkyl chains with a total of up to 18 carbon atoms, such as o-, m- and/or p-cresol, thymol, 4-tert.-butyl-phenol, 2,4,6-tri-tert.-butyl-phenol, n-nonylphenol, isononylphenol, isotridecyl-phenol, etc.

Among the aromatic compounds, there are preferred all the aromatic compounds having alcoholic hydroxyl groups, such as, for example, benzyl alcohol and all 2-hydroxyalkyl-ethers or -esters which are formed by oxalkylation reactions of phenolic hydroxy groups or of aromatic compounds containing carboxylic acid, phosphonic acid or phosphinic acid radicals, with compounds of the formulae IV or V.

For the preparation of aromatic starting compounds II with alcoholic hydroxyl groups there may therefore be mentioned, besides the aromatic compounds with phenolic hydroxyl groups already mentioned above, for the reaction with 1,2-alkylene oxides IV or 1,2-alkylene carbonates V, especially for example aromatic mono- and dicarboxylic acids, such as benzoic acid, phthalic acid, isophthalic acid, terephthalic acid, 1-naphthalene-carboxylic acid, naphthalene-carboxylic acid, the various naphthaline-dicarboxylic acids, but also aromatic hydroxy-carboxylic acids, such as the three different hydroxy-benzoic acids, the different naphthol-carboxylic acids, 4,4'-diphenyl-dicarboxylic acid, etc.

There are also suitable, for example, all the other aromatic carboxylic acids containing bromine, chlorine or fluorine, which are derived from benzene and naphthalene, such as - in particular-tetrabromo- and/or tetrachloro-phthalic acid and/or the anhydrides thereof. In this case, too, the reaction with compounds IV or V may be effected already in the presence of the compounds III, so that a corresponding process step may possibly be avoided, especially in the lay-out of technical processes.

In the same manner, aromatic phosphonic and/or phosphinic acids, such as benzene-phosphonic acid, 1,3-and/or 1,4-phenylene-diphosphonic acid, phenyl-methyl-phosphinic acid, 1,3-and/or 1,4-phenylene-bis-(methyl-phosphinic acid) may either be converted before into the corresponding 2-hydroxyalkylesters by a reaction with the 1,2-alkylene oxides IV and/or 1,2-alkylene carbonates V, or these acids and/or the many other suitable acids that have not been mentioned can be reacted in the reaction mixture directly with the 1,2-alkylene-oxides IV and/or 1,2-alkylene-carbonates V and the compounds III.

However, appropriate aromatic compounds with alcoholic hydroxyl groups may also be obtained by previous reactions of aromatic amines or mercapto compounds with 1,2-alkylene oxides and/or 1,2-alkylene-carbonates.

For these reactions, the following aromatic amines and/or mercaptans may be used in the form of compounds II Z(—X—H)$_n$. Naturally, they can also be used directly, i.e. without previous oxalkylation, due to their —XH-groups.

As compounds to be used which contain aromatic amino groups, there are to be mentioned, for example:

Aniline, methylaniline, o-, m-, p-phenylene-diamine, the various o-, m-, p-toluidines and -anisidines, -amino-phenols, -aminobenzoic acids, -aminobenzene-sulfonic acids, 1- and/or 2-naphthyl-amines, the various amino-naphthols, moreover, 4,4'-diaminodiphenylmethane, 4,4'-benzidine, the suitable chloro- and/or bromo-anilines and especially 2,4,6-tribromo-aniline, etc., but also phenylalkylamines, such as, above all, benzylamine or methyl-benzylamine and dibenzylamine.

As aromatic mercapto compounds there may be cited, for example:
phenylmercaptan, p-toluyl-mercaptan and/or 2-naphthyl-mercaptan, etc.

The suitable compounds III having the general formula

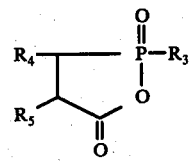

III include, for example, 2-methyl-, 2-ethyl-, 2-n-propyl-, 2-isobutyl-, 2-vinyl-, 2-chloromethyl-, 2-phenyl-, 2,3-dimethyl-, 2-methyl-3-ethyl, 2-methyl-3-butyl-, 2,4-dimethyl-, 2-methyl-4-ethyl-, 2-phenyl-4-methyl-, 2,3,4-trimethyl-, 2,3,4-triethyl-, but in particular - due to its easy preparation - 2-methyl-2,5-di-oxa-1,2-oxa-phospholane.

Appropriate 1,2-alkylene oxides of the formula IV are, for example, 1,2-butylene-oxide, 2,3-butylene oxide, but preferably epichlor hydrin, propylene oxide and especially ethylene oxide. Suitable 1,2-alkylene-carbonates of the formula V are, for example, propylene carbonate, 1,2-butylene-carbonate, 2,3-butylene-carbonate, 3-chloropropylene-carbonate and, preferably ethylene-carbonate.

The use of inert solvents and/or diluents is in most cases not required. However, there may be added, for example, acetone, methyl-ethyl-ketone, acetonitirle, 1,2-dichloroethane, benzene, toluene, xylene, chlorobenzene, but above all dioxane, if necessary, without any harm, as diluents and/or solvents, and these agents can be eliminated again by way of distillation still prior to the complete reaction with the 1,2-alkylene-carbonates V or at the very termination of the reaction.

The reaction temperatures for compounds II and III are in the range of from 0° to 180° C or higher, for example up to 250° C, preferably between 20° and 150° C, especially between 80° and 150° C. The reaction with the 1,2-alkylene-carbonates V is effected at a temperature of between about 80° and 250° C, preferably from 160° to 220° C, and with the 1,2-alkylene oxides at a temperature of from 80° to 180° C, preferably from 100° to 150° C. The reaction may be carried out stepwise in a way that at first 1 mole of the compounds II with $n$ -X-H-groups is reacted with 1 to $n$ moles of the "phospholanes" III and subsequently at first the same number of moles of compounds III and/or V act upon the mixture, until the acid number has been reduced to practically O. Afterwards the further moles of phospholane III and compounds IV and/or V are added in turns up to the desired final amount of $n \times m$ moles of the phhospholanes III and/or at least $n \times m$ moles of compounds IV and/or V, if neutral esters ($n \times m$) are to be obtained, or up to $n \times m (m+1)$ moles of phospholanes III and $n \times m$ moles of compounds IV and/or V, if products are desired that are still acid.

According to a preferred variant of the process, however, all $n \times (m+r)$ moles of the phospholanes III are introduced together with one mole each of the substances II containing $n$ —X—H— groups and — if acid final products ($r=1$) are to be obtained — together with $n \times m$ moles of the 1,2-alkylene-carbonates V and/or — to obtain neutral final products ($r=0$) — together with at least $n \times m$ moles of the compounds of formulae IV and/or V.

Due to by-reactions and impurities of the basis compounds II, the phospholanes III and/or the alkylene carbonates, it may be possible in may cases that more starting molecules are present than have been intended. This has the effect in some cases that the contents of hydroxyl groups found are slightly higher than have been calculated.

Depending on the value of $n$ and/or $m$ and on the type of compound Z(—X—H)$_n$ present, the compounds obtained are colorless and/or of a more or less yellowish shade and of a different consistency. If $n$ equals 1, —X— is oxygen or —S—, $R_3$ represents a lower alkyl radical and $R_4$ and/or $R_5$ are either also a lower alkyl radical or hydrogen, viscous liquids are obtained; if $n$ is 2, viscous oils are present in most cases, and if $n$ is 2, there are predominantly solid viscous masses, which are all well soluble in water, however.

If the molecular weight is increased by long chains, i.e. by high values of $m$, the viscosity is also increasing considerably.

Most compounds having NR$_1$-bridges are also solid, but water-soluble, with a varying water-solubility depending on the nature of Z. Aromatic basis substances, too, become water-soluble with values of $m$ exceeding approximatelay 3 or may be dispersed in water, even if they contain in addition other groups which strongly reduce the water-solubility, for example, halogen atoms, fluorine, chlorine or bromine.

Due to their relatively high phosphorus content, the compounds of formula I, especially the neutral and polyvalent compounds, are very well suitable as starting products for flameproofing agents or, in combination with cross-linking substances, directly as flameproofing agents that are fixable while being fast to washing, for example for textile goods. The application of these compounds is effected by impregnation of the textile material with a bath containing a compound of formula I, cross-linking compounds and a cross-linking catalyst, and by a subsequent cross-linking by a heat treatment.

As cross-linking components there may be mentioned polyfunctional N-methylol compounds, for example, derivatives of amino-1,3,5-triazines, such as trimethylol-melamine, hexamethylol-melamine, trimethylol-melamine-trimethylether, hexamethylol-melaminepentamethylether, trimethylol-melamine-triisobutylether, dimethylolaceto-guanamine, moreover, derivatives of urea, such as dimethylol-urea, dimethylol-urea-dimethylether, dimethylol-urea-dibutylether, dimethylol-cycloethylene-urea, dimethylol-cyclo-propyleneurea, dimethylol-4-methoxy-5-dimethyl-propylene-urea, dimethylol-5-hydroxypropylene-urea, 1,3-dimethylol-4,5-dihydroxy-imidazolidone-(2), 1,3-dimethylol-5-hydroxyethyl-hexahydrotriazine-on-(2), dimethylolurone and dimethylol-carbamates, such as dimethylolmethyl-carbamate, dimethylol-hydroxyethylcarbamate and dimethylol-methoxy-ethylcarbamate.

Interesting compounds which have proved to be particularly useful are the melamine derivatives, for example, trimethylolmelamine-trimethylether or hexamethylol-melamine-pentamethylether.

As catalysts which show their effect in the acid pH range, there are generally added from about 0.2 to 5% by weight, preferably from 0.4 to 3% by weight, of inorganic or oganic acids or their salts which set the acid free by hydrolysis or by a thermal treatment, for example, sulfuric acid, hydrochloric acid, phosphoric acid, trichloroacetic acid, maleic acid, tartaric acid, citric acid, acetic acid, or the salts thereof with ammonia, amines or polyvalent metals, preferably salts of strong acids or of medium strength, such as ammonium sulfate, ammonium chloride, mono- and diammonium oxalate, ammonium nitrate, magnesium chloride, aluminum chloride, zinc chloride, zinc nitrate, zinc fluoroborate, 2-amino-2-methyl-propanol-hydrochloride.

The cross-linking catalysts may be added to the finishing baths by themselves or in admixture with one another. These — preferably aqueous — finishing baths contain generally from 2 to 5% by weight, preferably from 2.5 to 4.5% by weight, of compounds of formula I, moreover, from 5 to 10% by weight, preferably from 7 to 9% by weight, of cross-linking substances as indicated above, furthermore from 0.2 to 5% by weight of cross-linking catalysts, as well as, optionally, from 5 to 25% by weight of high polymers, preferably in the form of dispersions.

The above-described phosphorus-containing compounds of formula I are water-soluble products or products that may be dispersed in water. They are added to the finishing baths in this form.

A special advantage of the compounds of the invention is to be seen also in their high stability, which involves a capacity of being stored for a long time also of aqueous concentrates as well as of aqueous finishing baths which already contain crosslinking agents and catalysts.

As textile fiber material there may be mentioned fibers and/or fabrics on the basis of native or regenerated cellulose or their mixtures. Very good permanent flameproof effects are obtained on synthetic fiber material or mixed fibers. As synthetic or mixed fiber material there are suitable, above all, non-woven fabrics, for example, needle felts for wall and floor coverings, textile wall coverings and air filters having a different composition, for example, needle felts of polyester-/polyamide-6-fibers in a 50/50 ratio, 100% polyamide fibers, 100% polyester fibers, polyamide fibers and viscose staple fibers in a 50/50 ratio, polyester fibers with viscose staple fibers in a 50/50 ratio or in a 75/25 ratio, polyamide/polyacrylonitrile/polyester fibers in a 50/25/25 ratio, glass fibers with polyester fibers in a 75/25 ratio, wool and polyamide fibers in a 50/50 ratio.

Suprisingly, the above-described phosphinic acid esters are also appropriate for the flameproof finishing of textile material made of polypropylene fibers or their mixtures with other synthetic or native or regenerated cellulose fibers, which could not be obtained so far in a satisfactory manner on the basis of phosphonic acid derivatives.

The process of the invention to impart a flameproof finish to textile materials is carried out under application conditions as they are common in the textile industry. The fabrics and/or needle felts are treated with the aqueous finishing baths on a two-roll and/or three-roll padding mangle, are squeezed off and subjected to a drying and/or condensation process. Fleeces that are bound by binding agents are either also finished on a padder or are hardened by being sprayed or foamed with the binding mixture.

For the flameproof finishing of cellulose fiber fabrics, the thermal treatment is carried out preferably in two steps. The material is at first dried at a temperature of more than about 50° C, preferably at about 100° C to 120° C, in order to eliminate the water to a residual value of from about 4 to 8%, and subsequently the condensation is allowed to take place at a temperature of from about 140° to 180° C, for approximately 7 to 3 minutes.

The flameproof finishing of needle felt covering material may also be effected according to the two-step process. However, in this case the cross-linking is preferably performed in a one-step drying and/or condensation process at a temperature of from about 120° to about 180° C, predominantly at 145° to 160° C. The heat treatment lasts for about 10 to about 60 minutes on an average, preferably from 20 to 30 minutes. The action of heat takes place in drying chambers, on stenter frames, hot flues or condensing stenters.

Further agents may be added to the finishing baths, such as textile softeners, products imparting water-repellent properties, products imparting oil-repellent properties, or also antimicrobial finishing products.

In order to improve the feel of cellulose fiber fabric, to ensure a good retention of shape, to improve the fasteness to rubbing and crushing of needle felt covering material, high polymer plastic materials may be added to the finishing baths, preferably in the form of plastic dispersions, for example on the basis of polyvinyl acetate, polyvinyl acetate with plasticizers, such as dibutyl-phthalate, copolymers of vinyl acetate with maleic acid-dibutylester, copolymers of acrylic acid-butylester with N-methylolacrylamide and acrylic acid, copolymers of acrylic acidbutyl-ester, N-methylolacrylamide and/or N-methylol-methacrylamide and acrylic acid, copolymers of acrylic acid-butylester, methacrylic acid-methylester and methylol-methacrylamide, copolymers of acrylic acid-butylester, acrylonitrile, N-methylolacrylamide and metahcrylic acid, copolymers of acrylic acid-butylester, acrylic acid-ethylester, acrylonitrile, N-methylol-methacrylamide and acrylic acid, copolymers of acrylic acid-butylester, styrene, acrylonitrile and N-methylol-methacrylamide, copolymers of N-methylol-methacrylamide and butanediol-diacrylate, acrylic acid-methyl-ester and acrylic acid-butylester, copolymers of ethyl-acrylate, acrylonitrile and N-methylolacrylamide, copolymers of butylacrylate, vinyl acetate with N-methylolacrylamide, copolymers of butylacrylate, acrylonitrile and N-methylolacrylamide, copolymers of styrene, butylacrylate and acrylic acid, natural latex or synthetic latices from styrene with butadiene.

Preferred polymer dispersions are polyvinyl acetate dispersions (of 50% strength), copolymers of vinyl acetate with maleic acid-dibutylester, for example in a ratio of 77/23 (about 50% strength), copolymers and styrene/butylacrylate/acrylonitrile/methacrylic acid/acrylamide, for example in a ratio of 16:61:25:2:1 or 25:53:25:2:1, copolymers of ethylacrylate/acrylonitrile/N-methylol-acrylamide 6:3:1, copolymers of butylacrylate/vinyl acetate/N-methylolacrylamide 35:55:10, furthermore, graft polymers (partially saponified), such as 50% polyvinyl alcohol, 25% polyvinyl acetate, 25% polyethylene oxide or butadiene-styrene latex (of about 50% strength), for example in a ratio of 40:60, 60:40 or 35:60 + 3.5 acrylic acid.

As compared with the commercial flameproofing agents on the basis of 3-(dimethyl-phosphono-)-propionic acid-amide, the products of the invention show great advantages especially with regard to permanence, to mention in particular the flameproof effect on polypropylene fibers or mixed fiber material and the excellent permanence especially after several commercial fine washings or shampooings.

Due to the very good flameproof effect of the compounds of the general formula I, the products may also be applied via the carpet back or via the pre-coating, and an ordinary bath finishing is therefore no longer required. This fact is of particular importance, since in the ordinary bath impregnation the pile thread, too, gets into contact with the flameproofing agents, cross-linking agents, binding agents on the basis of plastic dispersion and catalyts. In this treatment of the carpet pile, the flameproofing agents and the other components of the treatment bath are found on or between the pile threads, thus leading to agglutination. The individual thread of the pile should remain loose, however. Generally, an agglutination of the pile also results in a stronger soil deposition. Besides, the flameproofing agents may slowly be worn out by walking on the carpet.

The finish thus obtained is marked by its very good flameproof properties as well as by its very good permanence, for example, in shampooing and carpet washing processes.

The basic fabric of the carpets may consist of cotton, jute, viscose staple fiber, wool or synthetic fibers on the basis of polyamide or polyester, polypropylene or a mixture of the same, or of glass fibers. Needled fleece materials of polyester or polypropylene fibers are also excellently suitable for the process according to the invention.

The binding of the pile threads of a tufted material into the basic fabric, which may consist of natural or synthetic fibers or of needled fleeces of synthetic fibers, is effected by the so-called pre-coating with the commercial 40 to 50% plastic dispersions of the kind mentioned above.

Plastic dispersions of this nature are also used as back finish for woven carpets to impart a good feel in the hardening of the carpet.

Generally, a back coating with natural latex or synthetic latex dispersion, for example on the basis of butadiene and styrene 40:60 or 60:40, is effected subsequently in the case of tufted carpets.

As pile threads for tufted as well as woven carpets there may be mentioned fiber material of wool, polyamide, polyester and polyacrylonitrile. Fiber material of wool, polyamide or polyester threads having the common height of cut of 4 to 12 mm is preferably used.

The finishing baths for the pre-coating as well as for the back coating in the case of woven carpets contain in addition thickening agents.

As is already known, the thickening agent serves the purpose to put the finishing compositions into a physical state which prevents the impregnation baths from penetrating into the pile threads during application, thus agglutinating the same. As thickeners, there are suitable water-soluble hydroxyethylcelluloses, methyl celluloses, carboxylmethyl celluloses, water-soluble starch products, partially etherified or etherified starch products, polyvinyl alcohols, and the sodium or ammonium salts of alginic acid.

The pre-coating or the carpet back coating for woven carpets may besides be filled with chalk in a common manner.

The process for producing a flameproof finish in pile carpets by a carpet back treatment — a pre-coating or back coating — is carried out under the application conditions, as they are common in textile industry.

The pre-coating composition or the back finish in the case of woven carpets which contain the flameproof compound of formula I, the cross-linking agent and the catalyst, are applied by means of a skying doctor, a rubber squeeze or a cylinder doctor. Subsequently the material is dried and/or hardened on the stenter frame, in gelatinating or drying channels or in cylinder drying machines at a temperature of from 125° to 150° C. The dwelling time depends on the thickness of the carpets and is in the range of from 5 to 20 minutes, preferably 7 to 10 minutes. The back coating for tufted carpets is generally carried out by foaming the binding agent which contains the three components for the flameproof finish mentioned above. As cross-linking agents and catalysts there may be mentioned for this purpose the products that have been indicated further above.

When the burning and/or fire behavior of a tufted material is tested, which material has been finished with a flameproof agent according to the invention via the pre-coating and in addition is provided with a latex back coating, an excellent flameproof effect is surprisingly found for the entire carpet. The flameproof pre-coating forms a barrier layer towards the latex back so that the latter cannot be inflamed. It is therefore sufficient to incorporate the flameproof component into the pre-coating. In this case the latex back and the pile fibers do not require a flameproof finish. The compounds of the general formula I are marked by their high stability.

The said stability permits a prolonged storage of the finishing pastes ready to apply which contain, besides the flameproof agent, the cross-linking agent, the catalyst, the thickener and a latex dispersion. This flameproofing process is also distinguished by the fact that under the action of flames, no aggressive vapors in the form of hydrogen chloride or hydrogen bromide are formed, as this is the case to a large extent, if as flameproofing component there are used products on the basis of paraffin chloride, PVC, inorganic or organic bromine compounds.

In the following Examples there have been described at first two preparation processes to be applied generally for the reaction with alkylene oxides. The Examples carried out according to these processes as well as their results have been summarized in Tables A and B. In the Application Examples the use of the compounds thus obtained for textile finishing operations have further been indicated.

The Tables contain in their first column the serial number of the Examples, in the second column the chemical formula of the basis compound used. The third column gives the valency $n$ of this compound, and the following columns 4 to 6 show the amounts used of the three reactants as well as the pertinent mole numbers. As compound III there is generally used 2-methyl-2,5-dioxo-1-oxa-phospholane-2. In Examples (34)+ and (35)+, compound III stands for the corresponding 2,4-dimethyl-phospholane and in Example (61)+ for the corresponding 2-phenyl-phospholane.

As alkylene oxide IV there is generally used ehtylene oxide; in Example (36)× use is made instead of propylene oxide, and in Examples (37 to 40)+, of epichlorhydrin.

Column 7 contains once again a summary of the molar ratio figures, column 8 shows the amount and definition of a catalyst used, and column 9 gives the reaction temperature and/or time. In column 10, the acid number found of the final product has been indicated. As far as the consistency at room temperature (column 12) permitted a measuring of the refractive index, this latter value has been shown together with the corresponding temperature ( ° C) in column 11.

The yields and the phosphorus content of the products obtained practically correspond to the theoretical values and have thus not been included, for reasons of clearness.

In Example (30), 50 g of dioxan (indicated in column 8) were used as co-solvent.

EXAMPLES

A. General preparation method for Examples 1 through 50

(Table A)

At a reaction temperature of from about 80° to 130° C, $a$ moles (column 4) of the basis compounds of the formula II were introduced within about 5 to 20 minutes, optionally while drawing off the reaction heat, into $a \times n \times m$ moles (column 5) of the phospholanes III. In this case, $n$ stands for the number of —XH-groups (column 3) present in the basis compounds, and $m$ is the number of moles used per —XH-group of compound III (column 7). Subsequently, $a \times n \times m$ moles were either added at once, in the case of hardly volatile alkylene oxides IV, and were reacted during the reaction time, or at least $a \times n \times m$ moles were introduced in a gaseous state, without pressure, during the reaction time, in the case of more volatile alkylene oxides, especially with ethylene oxide which is mostly used, or were slowly added dropwise during the reaction time, while using a reflux condenser, in the case of other alkylene oxides having a low boiling point, for example, propylene oxide. In this process the gas introduction rate and/or dropping rate was controlled in accordance with the chemical reaction, so that practically no alkylene oxide was lost. The action of the easily volatile alkylene oxides was allowed to continue until the respective so-called acid number (consumption of mg of KOH per g of substance), which was determined in a 1:1 methanol-water mixture with phenolphthalein as indicator, had been reduced to less than about 12. Subsequently, all portions which were volatile under these conditions were eliminated under a reduced pressure of about 20 to 100 Torr at a temperature of from about 80° to 130° C. If alkylene oxides were used which were sufficiently volatile, the number of moles used was calculated from the difference between the input weight and the output weight. In order to characterize the compounds, the IR and the NMR spectrums were taken, the refractive indices (if possible), the acid numbers and the phosphorus contents were determined, with the latter naturally being almost fully in accordance with the contents calculated theoretically from the number of moles of III. The products obtained showed in the NMR spectrum characteristic multiplets at $\delta = 3.5 - 3.9$ and $\delta = 3.9 - 4.5$ which were lacking in the phospholanes used as starting compounds.

B. General preparation method for Examples 51 through 62

(Table B)

For the preparation of basis compounds of formula II in situ (cf. description on page 5), the same process as given in method A was applied with the difference that instead of the compounds of formula II, use was made of $a$ moles of phosphonic, phosphinic or carboxylic acids as starting compounds V (= preliminary stage) with $s$ acid final groups and $n'$ final groups of types (XH) of the invention in the molecule. In the mixture of these compounds with the corresponding phospholane and alkylene oxide, $a$ moles of compounds of formula II with $n = n' + s$ (column 3) were then formed in the first reaction step by the addition of one alkylene oxide each to an acid final group, which products continued to react, as has been described under A, with the phospholane of formula III and further alkylene oxide of the formula IV to give compounds of the formula I. The excess of alkylene oxide required as compared with method A for the formation of the compounds of formula II was $s$ moles of IV per mole of starting compound m i.e. $s \cdot a$ moles.

The 2-carboxyethyl-methyl-phosphinic acid used in Example 60 was prepared from the corresponding phospholane in situ by adding an adequate amount of water. The same was true for the 2-carboxy-ethyl-phenyl-phosphinic acid of Example 61.

| Example No. | Starting compound of formula II | n | II g (mole) |
|---|---|---|---|
| 1 | CH$_3$OH | 1 | 16.0 0.5 |
| 2 | CH$_2$=CH—CH$_2$OH | 1 | 29.0 0.5 |
| 3 | CH$_3$O—CO—CH$_2$OH | 1 | 45.0 0.5 |
| 4 | CH$_3$—CHOH—CH$_3$ | 1 | 15.0 0.25 |
| 5 | n-C$_4$H$_9$—CH(C$_2$H$_5$)—CH$_2$OH | 1 | 65.0 0.25 |
| 6 | final product of Example 4 | 1 | 121.5 0.25 |
| 7 | n-C$_{12}$H$_{25}$OH | 1 | 37.3 0.2 |
| 8 | HO—CH$_2$—CH$_2$OH | 2 | 232.8 3.6 |
| 9 | HOCH$_2$—CHOH—CH$_2$OH | 3 | 184.2 2.0 |
| 10 | HOCH$_2$—CHOH—CH$_2$OH | 3 | 9.2 0.1 |
| 11 | C$_2$H$_5$—C(—CH$_2$OH)$_3$ | 3 | 134 1.0 |
| 12 | C$_2$H$_5$—C(—CH$_2$OH)$_3$ | 3 | 11.2 0.083 |

-continued

| Example No. | Starting compound of formula II | n | II g (mole) |
|---|---|---|---|
| 13 | pentaerythritol | 4 | 13.6 0.1 |
| 14 | pentaerythritol | 4 | 3.5 0.025 |
| 15 | sorbitol | 6 | 12.2 0.067 |
| 16 | α-naphthol | 1 | 36.0 0.25 |
| 17 | 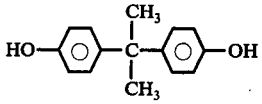 | 2 | 25.8 0.125 |

TABLE A

| Ex. | III g (mole) | IV g (mole) | molar ratio II:III:IV | catalyst | reaction temp. (°C) | time (h) |
|---|---|---|---|---|---|---|
| 1 | 167.4 1.25 | 55 1.25 | 1:2.5:2.5 | — | 125 | 13 |
| 2 | 134.1 1.0 | 44.4 1.01 | 1:2:2.02 | 1 g of sodium carbonate | 125 | 16 |
| 3 | 134.1 1.0 | 44.4 1.01 | 1:2:2.02 | — | 130 | 24 |
| 4 | 134.1 1.0 | 44.0 1.00 | 1:4:4.0 | — | 112 | 13 |
| 5 | 134.1 1.0 | 44.0 1.00 | 1:2:2.0 | — | 125 | 35 |
| 6 | 67.0 0.5 | 22.5 0.51 | 1:2:2.04 | — | 130 | 22 |
| 7 | 67.0 0.5 | 22.7 0.52 | 1:2.5:2.58 | — | 127 | 30 |
| 8 | 1931 14.4 | 670.7 15.26 | 1:4:4.24 | 0.6g of sodium carbonate | 125 | 20 |
| 9 | 1608.9 12.0 | 568 12.9 | 1:6:6.45 | — | 130 | 24 |
| 10 | 201.1 1.5 | 66 1.5 | 1:15:15.0 | — | 135 | 21 |
| 11 | 804.5 6.0 | 278 6.32 | 1:6:6.32 | — | 140 | 13 |
| 12 | 134.1 1.0 | 44 1.0 | 1:12:12.0 | — | 130 | 16 |
| 13 | 268.2 2.0 | 93.4 2.12 | 1:20:21.2 | — | 122 | 23 |
| 14 | 268.2 2.0 | 92.3 2.098 | 1:80:83.9 | — | 133 | 38 |
| 15 | 268.7 2.0 | 93.8 2.13 | 1:30:31.9 | — | 130 | 23 |
| 16 | 134.1 1.0 | 51.9 1.18 | 1:4:4.7 | — | 125 | 35 |
| 17 | 134.1 1.0 | 49.4 1.12 | 1:8:8.98 | — | 130 | 33 |

TABLE A

| Example No. | acid number found | $n_D^{°C}$ | consistency at room temperature |
|---|---|---|---|
| 1 | 0.5 | 1.4932 21 | oil |
| 2 | 0 | 1.4918 21 | oil |
| 3 | 5.7 | 1.4860 21 | oil |
| 4 | 1.5 | 1.4918 20 | oil |
| 5 | 5.0 | 1.4780 20 | oil |
| 6 | 6.0 | 1.4888 20 | oil |
| 7 | 4.5 | 1.4773 20 | viscous oil |
| 8 | 0 | 1.4966 21 | viscous oil |
| 9 | 3.2 | too viscous | solid |
| 10 | 4.8 | too viscous | solid |
| 11 | 1.4 | too viscous | solid |
| 12 | 7.0 | too viscous | solid |
| 13 | 6.1 | 1.4982 20 | solid |
| 14 | 5.5 | 1.4985 20 | solid |
| 15 | 1.8 | 1.5081 20 | solid |
| 16 | 4.4 | 1.5258 20 | solid |
| 17 | 4.2 | 1.5181 | solid |

TABLE A

| Example No. | Starting compound of formula II | n | II g (mole) |
|---|---|---|---|
| 18 | HO—C$_2$H$_4$—S—C$_2$H$_4$OH | 2 | 18.4 / 0.167 |
| 19 | N(—CH$_2$—CH$_2$—OH)$_3$ | 3 | 24.9 / 0.25 |
| 20 | polyethylene-glycol 600 (= average molar weight) | 2 | 150.0 / 0.25 |
| 21 | HO—⬡(H)—C(CH$_3$)(CH$_3$)—⬡(H)—OH | 2 | 40.1 / 0.167 |
| 22 | ⬡—OH | 1 | 47.1 / 0.5 |
| 23 | HOCH$_2$—P(=O)—(CH$_3$)$_2$ | 1 | 54 / 0.5 |
| 24 | HOCH$_2$—P(=O)—(CH$_3$)$_2$ | 1 | 21.6 / 0.2 |
| 25 | O=P—(CH$_2$OH)$_3$ | 3 | 15.64 / 0.111 |
| 26 | Cl—C$_2$H$_4$—OH | 1 | 40.3 / 0.5 |
| 27 | Br-⬡(Br,Br)—OH | 1 | 110.3 / 0.333 |
| 28 | HO—⬡(Br,Br)—C(CH$_3$)(CH$_3$)—⬡(Br,Br)—OH | 2 | 68.0 / 0.125 |
| 29 | HO—CH$_2$—CHBr—CHBr—CH$_2$OH | 1 | 62 / 0.25 |
| 30 | C$_6$F$_{13}$—C$_2$H$_4$—OH | 1 | 36.4 / 0.1 |
| 31 | Br-⬡(Br,Br,Br,Br)—OH | 1 | 61.1 / 0.125 |
| 32 | HO—⬡(Cl,Cl)—C(CH$_3$)(CH$_3$)—⬡(Cl,Cl)—OH | 2 | 45.8 / 0.125 |

TABLE A

| Ex. No. | III g (mole) | IV g (mole) | molar ratio II:III:IV | catalyst | reaction temp. (°C) | time (h) |
|---|---|---|---|---|---|---|
| 18 | 134.1 / 1.0 | 52.5 / 1.19 | 1:6:7.16 | — | 120 | 39 |
| 19 | 134.1 / 1.0 | 55 / 1.25 | 1:4:5.0 | — | 120 | 12 |
| 20 | 268.2 / 2.0 | 90 / 2.04 | 1:8:8.16 | — | 125 | 17 |
| 21 | 134.1 / 1.0 | 52.5 / 1.194 | 1:6:7.15 | 0.5 g of sodium carbonate | 135 | 11 |
| 22 | 201.2 / 1.5 | 89 / 2.02 | 1:3:4.04 | 2 g of sodium carbonate | 120 | 11 |
| 23 | 134.1 / 1.0 | 49 / 1.14 | 1:2:2.28 | — | 120 | 14 |
| 24 | 134.1 / 1.0 | 46.3 / 1.053 | 1:5:5.26 | — | 125 | 27 |
| 25 | 134.1 / 1.0 | 44.3 / 1.006 | 1:9:9.05 | — | 125 | 23 |
| 26 | 134.1 / 1.0 | 44.6 / 1.04 | 1:2:2.08 | — | 130 | 16 |
| 27 | 134.1 / 1.0 | 61 / 1.37 | 1:3:4.11 | 1 g of sodium carbonate | 120 | 8 |
| 28 | 134.1 / 1.0 | 46 / 1.045 | 1:8:8.36 | — | 135 | 29 |
| 29 | 134.1 / 1.0 | 47.5 / 1.08 | 1:4:4.32 | — | 120 | 28 |
| 30 | 84.4 / 0.6 | 29.2 / 0.66 | 1:6:6.63 | (50 g of dioxan) | 102 | 27 |
| 31 | 134.1 / 1.0 | 52.8 / 1.20 | 1:8:9.6 | — | 130 | 23 |
| 32 | 134.1 / 1.0 | 50.1 / 1.14 | 1:8:9.11 | — | 128 | 39 |

TABLE A

| Example No. | acid number found | $n_D$ °C | consistency at room temperature |
|---|---|---|---|
| 18 | 8.0 | 1.5118 / 20 | very viscous |
| 19 | 6.2 | 1.4878 / 20 | oil |
| 20 | 2.6 | 1.4896 / 20 | oil |
| 21 | 1.5 | 1.5039 / 20 | very viscous |
| 22 | 0 | 1.5112 / 21 | oil |
| 23 | 1.3 | — | liquid |
| 24 | 2.9 | 1.5032 / 20 | oil |
| 25 | 12.0 | 1.5005 / 20 | solid |
| 26 | 0.8 | 1.4934 / 20 | oil |
| 27 | 1.5 | too viscous | solid |
| 28 | 12.4 | too viscous | solid |
| 29 | 5.2 | 1.4985 / 25 | oil |
| 30 | 1.7 | too viscous | solid |
| 31 | 10.0 | too viscous | solid |
| 32 | 13.0 | 1.5626 / 20 | solid, viscous |

TABLE A

| Example | Starting compound of the formula II | n | II g (mole) |
|---|---|---|---|
| 33 | HO—C$_2$H$_4$—O—⬡(Br,Br)—C(CH$_3$)(CH$_3$)—⬡(Br,Br)—OC$_2$H$_4$OH | 2 | 63.2 / 0.1 |
| 34[+)] | HOCH$_2$—CHOH—CH$_2$OH | 3 | 7.36 / 0.08 |
| 35[+)] | CH$_2$Br—CHBr—CH$_2$OH | 1 | 54.5 / 0.25 |
| 36[x)] | HO—CH$_2$—CH$_2$—OH | 2 | 15.5 / 0.25 |
| 37[x)] | HO—CH$_2$—CH$_2$—OH | 2 | 31 / 0.5 |
| 38[x)] | HO—CH$_2$—CH$_2$—OH | 2 | 62 / 1.0 |
| 39[x)] | HOCH$_2$—CHOH—CH$_2$OH | 3 | 30.7 / 0.333 |
| 40[x)] | HO—(C$_2$H$_4$—O)$_n$H average: n=13 | 2 | 150 |

TABLE A-continued

| Example | Starting compound of the formula II | n | II g (mole) |
|---|---|---|---|
| | mole=600 | | 0.25 |
| 41 | H$_2$N—C$_2$H$_4$—NH$_2$ | 2 | 25 |
| | | | 0.42 |
| 42 | HN—[CH—(CH$_3$)$_2$]$_2$ | 1 | 25.3 |
| | | | 0.25 |
| 43 | ⌬—NH$_2$ | 1 | 23.3 |
| | | | 0.25 |
| 44 | HN—(CH$_2$—⌬)$_2$ | 1 | 98.6 |
| | | | 0.5 |
| 45 | Br-substituted H$_2$N—⌬—Br with Br | 1 | 82.5 |
| | | | 0.25 |
| 46 | H$_2$N—⌬—NH$_2$ | 2 | 27 |
| | | | 0.167 |
| 47 | H$_2$N—⌬—⌬—NH$_2$ | 2 | 27 |
| | | | 0.147 |

TABLE A

| Example No. | III g (mole) | IV g (mole) | molar ratio II:III:IV | catalyst | reaction temp. (° C) | time (H) |
|---|---|---|---|---|---|---|
| 33 | 134.1 / 1.0 | 45.3 / 1.03 | 1:10:10.3 | — | 130 | 11 |
| 34+) | 71 / 0.48 | 25 / 0.57 | 1:6:7.13 | 0.5 g of sodium carbonate | 130 | 8 |
| 35+) | 74 / 0.5 | 30 / 0.68 | 1:2:2.72 | — | 130 | 20 |
| 36×) | 134.1 / 1.0 | 67 / 1.15 | 1:4:4.6 | 0.5 g of sodium carbonate | 145 | 22 |
| 37×) | 134.1 / 1.0 | 101.6 / 1.1 | 1:2:2.2 | — | 135 | 14 |
| 38×) | 536.4 / 4.0 | 406.4 / 4.4 | 1:4:4.4 | 2 g of sodium carbonate | 130 | 8 |
| 39×) | 268.2 / 2.0 | 231 / 2.5 | 1:6:7.5 | — | 125 | 10 |
| 40×) | 134.1 / 1.0 | 101.8 / 1.1 | 1:4:4.4 | — | 138 | 9 |
| 41 | 402 / 3 | 159 / 3.62 | 1:7.14:8.6 | — | 130 | 35 |
| 42 | 134.1 / 1.0 | 44.6 / 1.01 | 1:4:4.056 | — | 120 | 32 |
| 43 | 134.1 / 1 | 47.6 / 1.08 | 1:4:4.32 | — | 125 | 28 |
| 44 | 201.2 / 1.5 | 66.1 / 1.51 | 1:3:3.02 | — | 128 | 17 |
| 45 | 134.1 / 1.0 | 55.5 / 1.26 | 1:4:5.04 | — | 125 | 24 |
| 46 | 134.1 / 1.0 | 45.9 / 1.043 | 1:6:6.25 | — | 130 | 17 |
| 47 | 134.1 / 1.0 | 51.9 / 1.18 | 1:7.7:8.02 | — | 140 | 28 |

TABLE A

| Example No. | acid number found | $n_D$ ° C | consistency at room temperature |
|---|---|---|---|
| 33 | 0.8 | 1.5188 / 20 | solid |
| 34+) | 0 | too viscous | solid |
| 35+) | 2.7 | 1.4955 / 25 | oil, very viscous |
| 36×) | 0 | — | very viscous oil |
| 37×) | 3.1 | too viscous | solid, viscous |
| 38×) | 4.0 | too viscous | solid, viscous |
| 39×) | 22 | very viscous | solid, viscous |
| 40×) | 10.0 | 1.4942 / 20 | viscous oil |
| 41 | 10 | 1.4972 / 25 | oil, very viscous |
| 42 | 14.3 | 1.4953 / 20 | oil, very viscous |
| 43 | 2.5 | 1.5247 / 20 | oil, very viscous |
| 44 | 10.3 | too viscous | very viscous |
| 45 | 3.7 | too viscous | solid |
| 46 | 7.5 | too viscous | solid |
| 47 | 1.4 | too viscous | solid |

TABLE A

| Example No. | Starting compound of formula II | n | II g (mole) |
|---|---|---|---|
| 48 | H$_2$N—C$_2$H$_4$—OH | 2 | 15.3 / 0.25 |
| 49 | C$_{12}$H$_{24}$—SH | 1 | 67.3 / 0.33 |
| 50 | ⌬—SH | 1 | 18.4 / 0.167 |

TABLE B

| Example No. | Starting compound of formula II | n | II g (mole) |
|---|---|---|---|
| 51 | HO−P(CH₃)(=O)−CH₂−CH₂−P(CH₃)(=O)−OH | 2 (2) | 93 0.5 |
| 52 | (HOOC−C₂H₄)₂−P(=O)−OH | 3 (3) | 20.8 0.1 |
| 53 | HO−P(CH₃)(=O)−C₆H₄−P(CH₃)(=O)−OH | 2 (2) | 14.05 0.06 |
| 54 | HO−CO−C₆H₄−P(CH₃)(=O)−OH | 2 (2) | 20 0.1 |
| 55 | HO−P(=O)−C(CH₃)(C₂H₅)(OH)−P(=O)−OH | 3 (2) | 28.5 0.15 |
| 56 | CH₃−P(=O)(OH)₂ | 2 (2) | 48 0.5 |
| 57 | CH₂=CH−P(=O)(OH)₂ | 2 (2) | 54 0.5 |
| 58 | n-C₈H₁₇−P(=O)(OH)₂ | 2 (2) | 32.4 0.167 |

TABLE A

| Ex. No. | III g (mole) | IV g (mole) | molar ratio II:III:IV | catalyst | reaction temp. (°C) | time (h) |
|---|---|---|---|---|---|---|
| 48 | 134.1 1.0 | 49.6 1.13 | 1:4:4.52 | — | 125 | 16 |
| 49 | 134.1 1.0 | 64.7 1.47 | 1:3:4.41 | 1 g of sodium carbonate | 115 | 9 |
| 50 | 134.1 1.0 | 52.5 1.19 | 1:6:7.14 | — | 120 | 39 |

TABLE B

| Ex. No. | III g (mole) | IV g (mole) | molar ratio II:III:IV | catalyst | reaction temp. (°C) | time (H) |
|---|---|---|---|---|---|---|
| 51 | 268.2 2.0 | 139 3.16 | 1:4:6.32 | — | 125 | 19 |
| 52 | 120.6 0.9 | 52.6 1.2 | 1:9:12.0 | — | 135 | 26 |
| 53 | 48.2 0.36 | 21.1 0.48 | 1:6:8.0 | — | 125 | 10 |
| 54 | 134.1 1.0 | 65 1.48 | 1:10:14.8 | — | 115 | 20 |
| 55 | 120.8 0.9 | 68.9 1.56 | 1:6:10.4 | — | 130 | 30 |
| 56 | 268.2 2.0 | 142.3 3.23 | 1:4:6.46 | — | 125 | 13 |
| 57 | 268.2 2.0 | 145 3.3 | 1:4:6.6 | — | 120 | 28 |
| 58 | 134.1 1.0 | 61.5 1.4 | 1:4:8.4 | — | 120 | 36 |

TABLE A

| Example No. | acid number found | $n_D$ °C | consistency at room temperature |
|---|---|---|---|
| 48 | 0 | 1.5035 20 | oil, very viscous |
| 49 | 1.5 | 1.4899 20 | oil, very viscous |
| 50 | 6.5 | 1.5118 | oil, very viscous |

TABLE A-continued

| Example No. | acid number found | $n_D$ °C | consistency at room temperature |
|---|---|---|---|
| | | 29 | |

TABLE B

| Example No. | acid number found | $n_D$ °C | consistency at room temperature |
|---|---|---|---|
| 51 | 6.0 | — | solid |
| 52 | 5.9 | — | solid |
| 53 | 0 | — | solid |
| 54 | 0 | — | solid |
| 55 | 10.3 | 1.4794 21 | viscous oil |
| 56 | 9.5 | — | oil |
| 57 | 9.5 | — | oil |
| 58 | 3.0 | 1.4921 20 | oil |

TABLE B

| Example No. | Starting compound V | n (s) | V g (mole) |
|---|---|---|---|
| 59 | CH₂=CBr−P(CH₃)(=O)−OH | 1 (1) | 18.5 0.1 |
| 60 | HO−P(CH₃)(=O)−CH₂−CH₂−COOH | 2 (2) | 15.2 0.1 |
| 61⁺⁾ | HO−P(C₆H₅)(=O)−CH₂−CH₂−COOH | 2 (2) | 13.06 0.061 |
| 62 | Br₄C₆(COOH)(COOC₂H₄OH) | 2 (1) | 105.1 0.1 |

TABLE B

| Example No. | III g (mole) | IV g (mole) | molar ratio V:III-IV | catalyst | reaction temp. (°C) | time (h) |
|---|---|---|---|---|---|---|
| 59 | 134.1 1.0 | 53.2 1.29 | 1:10:12.1 | — | 125 | 23 |
| 60 | 120.8 0.9 | 48.9 1.11 | 1:9:11.1 | — | 145 | 13 |
| 61⁺⁾ | 48 0.245 | 16.2 0.37 | 1:4:6.1 | — | 130 | 24 |
| 62 | 107.2 0.8 | 68.7 1.56 | 1:4:7.8 | — | 135 | 12 |

TABLE B

| Example No. | acid number found | $n_D$ °C | consistency at room temperature |
|---|---|---|---|
| 59 | 8.9 | 1.5027 20 | viscous oil |
| 60 | 8.4 | — | solid |
| 61⁺⁾ | 2.3 | — | solid |
| 62 | 0.9 | — | solid |

EXAMPLE 63: (stepwise reaction)

(a₁.₁) In a four-neck flask provided with stirrer, thermometer, reflux condenser and gas inlet tube, 134.1 g (1 mole) of 2-methyl-2,5-dioxo-1-oxa-phospholane-2 were heated to 110° C, while extremely pure nitrogen was passed over the same. Within 25 minutes, 104.2 g (1 mole) of methyl-diglycol (CH$_3$—O—C$_2$H$_4$—O—C$_2$H$_4$—OH) were added dropwise under air cooling. The reaction temperature was maintained between 110° and 118° C.

After the phospholane peak at 5.5 μ had disappeared, the mixture was cooled. The output weight was 238.3 g, the acid number 248.8 (calculated: 235.0), the refractive index $n_D^{20}$ = 1.4706, the P-content 13.0% (calculated: 13.0%).

(a$_{2.1}$) At a temperature of from 128 to 132° C, 45.7 g (1.037 moles) of alkylene oxide were introduced in the gaseous state within 24 hours, while stirring vigorously, without pressure, into 238 g (1 mole) of the "acid (1)" obtained according to (a$_{1.1}$) of the formula

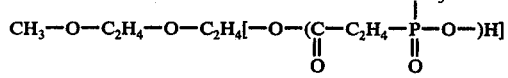

in the same rate in which it was consumed. In the course of this process, the acid number was reduced to 2.8. After the introduction had been completed, volatile compounds were drawn off during 30 minutes at 110° C, under a pressure of 30 Torr. The output weight was then 284 g, the refractive index $n_D^{20}$ was 1.4724, the P-content 10.9% (calculated: 10.9%).

(a$_{1.2}$) According to (a$_{1.1}$) at a temperature of about 125° C, 67 g (0.5 mole) of the phospholane were added within 5 minutes to 142 g (0.5 mole) of the "ester (1)" obtained according to (a$_{2.1}$) of the formula

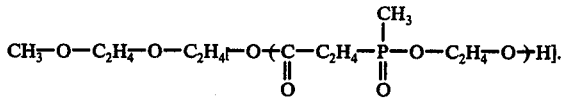

The output weight was 201 g, the acid number 145.6 (calculated: 134.0), the refractive index $n_D^{20}$ was 1.4875, the P-content 14.8% (calculated: 14.8%).

(a$_{2.2}$) According to process (a$_{2.1}$) at a reaction temperature in the range of from 128° to 132° C, 22 g (0.5 mole) of ethylene oxide were introduced within 26 hours into 200 g (0.5 mole) of the "acid (2)" thus obtained of the formula

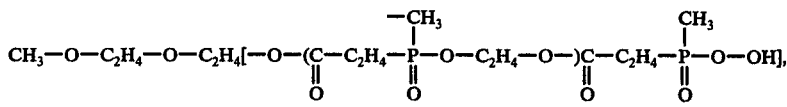

and upon completion of the reaction, easily volatile compounds were drawn off. The output weight was 231 g, the acid number was 2.7, the refractive index $n_D^{20}$ was 1.4831, and the P-content 13.4% (calculated: 13.4%).

(a$_{1.3}$) At 120° C, 115.5 g (0.25 mole) of the "ester (2)" thus obtained of the formula

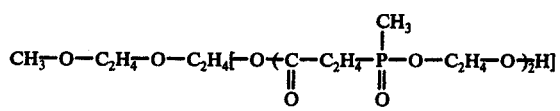

were reacted with 33.5 g (0.25 mole) of the phospholane according to process (a$_{1.1}$). The output weight was 149 g, the acid number 96.8 (calculated: 94.0), the refractive index $n_D^{20}$ was 1.4922 and the P-content 15.6% (calculated: 15.6).

(a$_{2.3}$) At a temperature of 130° C, 11.0 g (0.25 mole) of ethylene oxide were introduced, according to process (a$_{2.2}$) into 149 g of the "acid (3)" thus obtained which had the formula

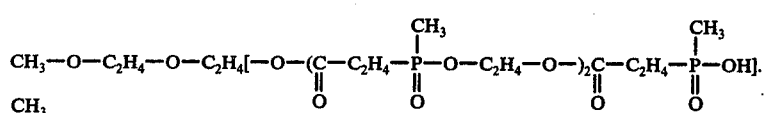

160 Grams of the "ester (3)" of the formula

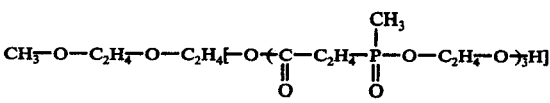

were obtained. The acid number of the product was 5.8, the refractive index $n_D^{20}$ was 1.4839, and the P-content 14.5% (calculated: 14.5%).

The compounds thus obtained were at room temperature oils showing a slightly yellow color shade.

EXAMPLE 64

1287 Grams (9.6 moles) of 2-methyl-2,5-dioxo-1-oxa-phospholane-2 were introduced into a V4A autoclave having a capacity of 3 liters and were heated, while nitrogen was passed over, to a temperature of 120° C. Subsequently, 149 grams (2.4 moles) of glycol and 0.6 gram of sodium carbonate were added as catalysts within 40 minutes. At a temperature of from 135° to 140° C, 423 grams (9.61 moles) of liquid ethylene oxide were pressed in with nitrogen as auxiliary gas, while stirring rapidly, within 3 hours and at a pressure being formed which was in the range of from 2.8 to 3 atmospheres. The mixture was continued to be stirred for another hour, was cooled to 110° C, the tension was released to normal pressure, and the contents of the autoclave were evacuated.

As a result, 1869 g of an oil showing a slightly yellow color shade were obtained, which oil had the acid number of 1.8. A P-content of 15.9% was determined (calculated: 16.0%); $n_D^{22}$ = 1.4969.

C. General preparation method for Examples 65 through 76

(Table C)

At room temperature, $a$ moles (column 4) of the basis compounds of formula II were added to at least $a \times n \times m$ moles (column 6) of the 1,2-alkylene carbonates of the formula V, and another $a \times n \times m$ moles (column 5) of 2,4-dioxo-2-methyl-1-oxaphospholane, in short termed "phospholane" were added. After the addition of $b$ grams of an alkali metal catalyst (column 8) the mixture was heated and was maintained for $c$ hours (column 10) at the reaction temperature $d$ (column 9). In the course of this process, at least $a \times n \times m$ moles of carbon dioxide escaped, according to the amount of 1,2-alkylene carbonate V (column 6) added, which could be detected for example quantitatively by means of a gas meter and/or qualitatively by way of a simple bubble counter. After the termination of the carbon dioxide development the reaction mixture was cooled, and the output weight as well as the acid number and — if possible — the refractive index ($n_D$) were determined. As to their IR and NMR spectra and their other physical and chemical properties and those with respect to application in technology the reaction products corresponded to those compounds that had been prepared with alkylene oxides. In Examples 65 through 75, the 1,2-alkylene carbonate V was identical with ethylene carbonate, in Example 76 with 1,2-propylene carbonate.

General preparation method for Examples 65 through 76

(Table D)

In order to prepare the basis compounds of formula II in situ, the same process was applied as in method C with the difference that instead of the compounds of formula II, use was made of $a$ moles of phenols, phosphonic, phosphinic or carboxylic acids as starting compounds with $s$ phenolic or acid terminal groups and $n'$ terminal groups of the type (XH) of the invention in the molecule. In the first reaction step, $a$ moles of compounds of the formula II with $n \times n' + s$ (column 3) were formed in the mixture of these compounds with the respective phospholane III and 1,2-alkylene carbonate V, by the addition of one 1,2-alkylene carbonate each to a phenolic or acid terminal group, which products continued to react, as has been described under A, with the phospholane of the formula III and a further amount of 1,2-alkylene carbonate of the formula V to give compounds of formula I with primary alcohol groups. The excess amount of 1,2-alkylene carbonate V required in contrast to method C for the formation of the said compound of the formula II was $a$ moles per mole of starting compound, i.e. $s \cdot a$ moles.

The 2-carboxyethyl-methyl-phosphinic acid used in Example 81 was produced in the form of its di-sodium salt from the corresponding phospholane in situ by the addition of an adequate amount of sodium carbonate.

The phosphonic acid-semi-ester of Example 82 was used from the start in the form of the sodium salt.

TABLE D

| Example | Starting compound of the formula II | n (s) | II g (a moles) | III g (axnxm moles) | V g (mole) | molar ratio II:III:IV | catalyst (g) | reaction temp. (°C) | reaction time (h) | acid number found | $n_D^{°C}$ | consistency at room temperature |
|---|---|---|---|---|---|---|---|---|---|---|---|---|
| 77 | 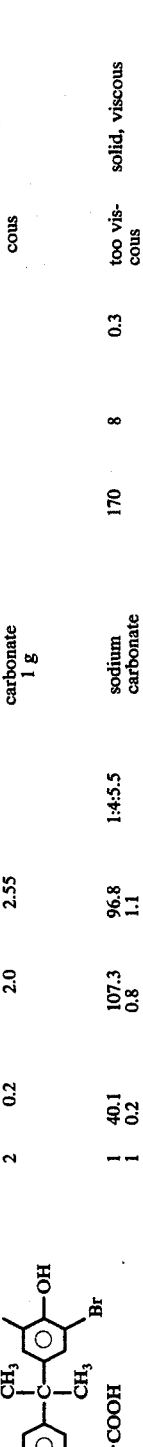 | 2 2 | 108.8 0.2 | 168.2 2.0 | 224.0 2.55 | 1:10:12.75 | sodium carbonate 1 g | 185 | 5 | 0.5 | too viscous | viscous |
| 78 | $C_{11}H_{23}$—COOH | 1 1 | 40.1 0.2 | 107.3 0.8 | 96.8 1.1 | 1:4:5.5 | sodium carbonate 0.5 | 170 | 8 | 0.3 | too viscous | solid, viscous |
| 79 | 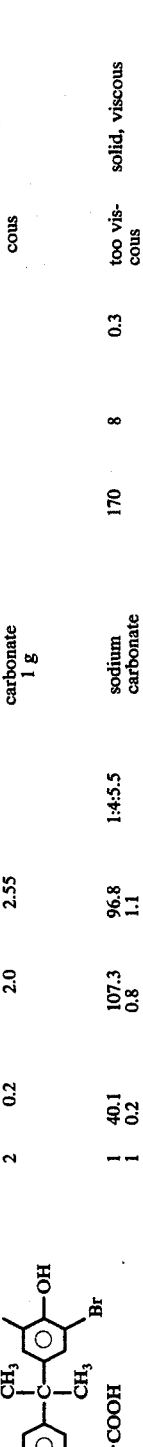 | 2 2 | 19.4 0.1 | 107.3 0.8 | 96.8 1.1 | 1:8:11 | sodium carbonate 0.5 | 190 | 9 | 1.2 | too viscous | solid, viscous |
| 80 | 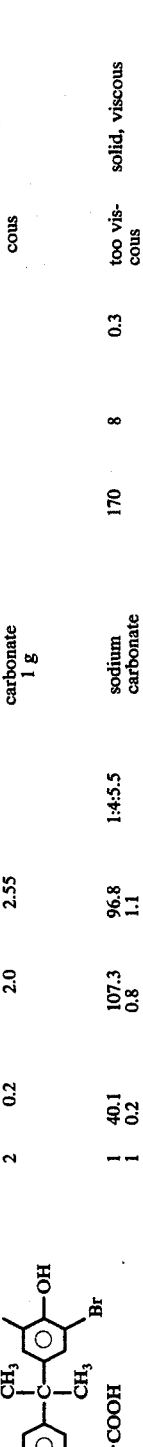 | 2 2 | 18.6 0.1 | 134.1 1.0 | 114.4 1.1 | 1:10:13 | potassium carbonate 1.0 | 185 | 6 | 8.6 | too viscous | solid, viscous |
| 81 | 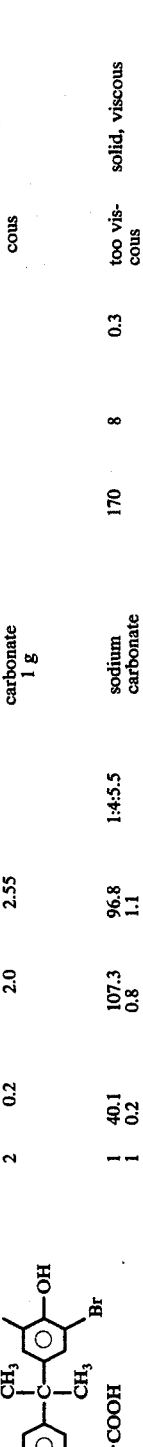 | 2 2 | 3.8 0.025 | 134.1 1.0 | 92.4 1.05 | 1:4:42 | contained in II | 190 | 4 | 2 | too viscous | solid, viscous |
| 82 | 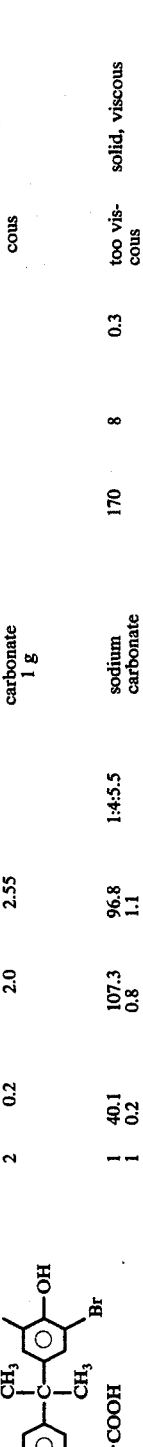 | 1 1 | 17.4 0.1 | 1341 1 | 96.8 1.05 | 1:10:11 | contained in II | 180 | 5 | 4.3 | 1.4941 40 | highly viscous |

EXAMPLE 83: (Step-by-step process)

31 g (0.5 mole) of ethylene glycol,
88.1 g (1.0 mole) of ethylene carbonate,
134.1 g (1.0 mole) of 2,5-dioxo-2-methyl-1,2-oxophospholane ("phospholane") and
1.0 g of sodium carbonate (as catalyst) were heated to 185° C, while stirring, and were maintained for 8 hours at this temperature. In the course of this process, 44 g (1.0 mole) of carbon dioxide escaped. The acid number was 12.3. The refractive index $n_D^{20}$ was 1.4928. After the addition of further
105.6 g (1.2 moles) of ethylene carbonate and
134.1 g (1.0 mole) of "phospholane", the mixture was again heated for 6 hours at 190° C, with further 52.7 g (1.2 moles) of carbon dioxide escaping in the process. After cooling,
396 g of reaction product were left, which had an acid number of 4.6 and a refractive index $n_D^{20}$ of 1.4989.

EXAMPLES OF APPLICATION

EXAMPLE I

A coarse-threaded needle felt floor covering consisting of a polyester fiber core and a polyamide upper surface in the ratio of 65 : 35 was treated on a two-roll padding mangle with an aqueous solution having the following composition:

350 g/l of a reaction product of 1 mole of glycol, 4 moles of phospholane and 4.3 moles of ethylene oxide analogous to Example 8, furthermore, 160 g/l of trimethylol-melamine-trimethylether, 3.5 g/l of zinc chloride, 200 g/l of a 40% plastic dispersion of ethyl acrylate/acrylonitrile/N-methylolacrylamide copolymer in the ratio of 6:3:1.

The squeezing-off effect was 100%. Subsequently the material was dried for 25 minutes at 140° C.

The needle felt showed a very good retention of shape and elasticity and also had a very good capacity of being reeled off.

The needle felt showed a very good flameproof effect which lasted for several shampooings and fine washings up to 50° C.

The flameproofing test was effected according to DIN (German Industrial Standard) 54 333, with a determination of the flame spreading rate of textile materials, or according to US Motor Vehicle Safety Standard No. 302 (US-MVSS 302).

When the test sample was only finished with 200 g/l of the plastic dispersion mentioned in the Example, it continued to burn in full width after removal of the flame source. The flame front covered a measuring distance of 10 cm within a time of 3 minutes and 35 seconds. In contradistinction thereto, the needle felt material finished according to the invention did not continue to burn after removal of the test flame. Only an after-burn effect could be found outside the measuring distance, which lasted for 3 to 8 seconds. After two fine washings with 2 g/l of a commercial high-duty detergent (washing time 15 minutes each time at 40° C), the needle felt did not continue to burn either following the removal of the flame source. The after-burn period had only been increased to 25 to 50 seconds. Also after the fifth shampooing, the needle felt did not continue to burn either. The after-burn effect again lasted for only 45 seconds.

EXAMPLE II

The needle felt described in Example I was treated according to the same application process with the aqueous impregnation bath indicated below:

400 g/l of a reaction product of 1 mole of glycerol, 6 moles of phospholane and 6.45 moles of ethylene oxide (analogous to Example 9), 160 g/l of trimethylol-melamine-trimethylether, 4 g/l of zinc chloride, 200 g/l of a 40% plastic dispersion of ethylene acrylate/acrylonitrile/N-methylolacrylamide (6:3:1) copolymer.

The squeezing-off effect was 95%. Subsequently the material was dried for 25 minutes at 145° C in a drying cabinet with circulating air and was hardened at the same time.

The needle felt showed a very good permanent flameproof effect which lasted for several wet treatments (shampooings or fine washings at 40° C).

The feel was elastic, and the needle felt showed a good retention of shape, which was still excellent after several wet treatments.

Instead of 160 g/l of trimethylol-melamine-trimethylether, there may also be used as cross-linking component of the terminal hydroxyl groups of the phosphinic acid ester being present, 250 g/l of a 50% dimethylol-dihydroxyethylene-urea solution. The needle felt thus finished also showed a permanent flameproof effect as well as a good retention of shape.

EXAMPLE III

A needle felt floor covering having a weight of 700 g per square meter and consisting of a fine-threaded polypropylene core and a coarse-threaded upper surface of polypropylene fibers was treated on a two-roll padder with the aqueous impregnation solution which had been described in Example I.

The squeezing-off effect was 100%. Subsequently the material was treated for 30 minutes at 135° C.

The flameproof effect was excellent, it remained unaltered even after several wet treatments. The feel was very flexible, and the needle felt maintained its retention of shape also after having been subjected to wet treatments. The very smooth feel of the polypropylene fiber was improved by the finish and became more textile.

EXAMPLE IV

Similar good effects were also obtained on the needle felt described in Example III, if the finishing was carried out according to the specification given in Example II, i.e. with a reaction product of 1 mole of glycerol, 6 moles of phospholane and 6.45 moles of ethylene oxide and the additional and/or cross-linking components described.

The dyring and/or condensation was carried out at 135° C.

EXAMPLE V

A needle felt covering used in the automobile industry which was designed for covering the trunk compartment and the passenger room and which consisted of 50% of fine-threaded polyamide fibers and 50% of viscose staple fibers having a weight per square meter of 550 g, was impregnated with a solution containing 300 g/l of the reaction product of 1 mole of glycol, 4 moles of phospholane and 4.3 moles of ethylene oxide (analogous to Example 8), 120 g/l of hexamethylol-melamine-pentamethylether, 180 g/l of a 50% polyvinylacetate dispersion and 5 g/l of ammonium chloride. The treatment was effected on a two-roll padder with a squeezing-off effect of 95%. The material was then subjected to drying and condensation in a drying cabinet for 25 minutes at 150° C.

The needle felt showed a pronounced permanent flameproof effect. It was flexible and could well be pasted on metal sheets.

EXAMPLE VI

A textile wall covering which consisted of 25% of polyester fibers and 75% of glass fibers and which was to serve as covering fabric for a flameproof polyurethane foam was treated with an impregnation solution, as has been described in Example II, in a way that it was drawn off from an impregnation solution via a steel roller. As counter roller there was used a rubber roller which was besides wrapped with a cotton knitted fabric (lapping). The liquor pick-up was 150%. After a drying period of 10 minutes at 150° C, a textile wall covering was obtained which was non-slipping andd flameproof to an excellent degree.

EXAMPLE VII

An impregnation solution contained 300 g/l of a reaction product of 1 mole of pentaerythritol, 20 moles of phospholane and 21.4 moles of ethylene oxide (analogous to Example 13). The phosphorus content of the reaction product was about 15.6%.

As cross-linking component, 100 g/l of hexamethylol-melamine-pentamethylether were added as well as 5 g/l of ammonium chloride as catalyst. A fine-threaded polyester needle felt having a weight per square meter of 350 g was treated with the impregnation solution described on a two-roll padder. It was squeezed off to a liquor pick-up of 100%, then dried at 145° C. The needle felt which had very good flameproof properties was suitable as insulating material for building protection.

EXAMPLE VIII

A needle felt floor overing consisting of 50% of polyamide and 50% of polyester fibers and having a weight per square meter of 650 g was treated with the aqueous impregnation solution specified below:

400 g/l of a reaction product of 1 mole of trimethylolpropane, 12 moles of phospholane and 12 moles of ethylene oxide, 180 g/l of a 80% trimethylol-melamine-trimethylether solution, 250 g of a 50% polyvinylacetate dispersion and 20 g/l of a 40% 2-amino-2-methyl-propanol-hydrochloride solution.

After the treatment on a two-roll padder with a squeezing-off effect of 105% and drying period of 25 minutes at 145° C, a needle felt was obtained which ahd a flexible feel and which showed excellent flameproof properties.

EXAMPLE IX

The needle felt described in Example I was treated with an aqueous finishing bath having the composition specified below, on a two-roll padder:

350 g/l of a reaction product of 1 mole of benzoic acid, 6 moles of phospholane and 6.6 moles of ethylene oxide, 100 g/l of hexamethylol-melamine-pentamethylether, 20 g/l of a 40% 2-amino-2-methyl-propanol-hydrochloride solution, and 200 g/l of a 40% plastic dispersion of ethylacrylate/acrylonitrile/N-methylolacrylamide (6:3:1) copolymer.

The squeezing-off effect was about 105%. Subsequently the material was dried for 25 minutes at 140° C in a laboratory drying cabinet with circulating air and hardened.

EXAMPLE X

A polypropylene needle felt consisting of a fine-threaded core and a coarse-threaded upper surface and having a weight per square meter of 750 g was treated on a two-roll padder with an aqueous impregnation solution which contained 320 g/l of a reaction product of 1 mole of lactic acid-methylester with 2 moles of phospholane and 2.02 moles of ethylene oxide; 120 g/l of hexamethylol-melamine-pentamethylether;

5 g/l of ammonium chloride and 200 g/l of a 40% plastic dispersion, as has been described in Example IX.

The squeezing-off effect was 100%. The material was dried according to Example IX, however, only at 175° C.

The needle felt thus treated had a good retention of shape, was flexible and was marked by a very good permanent flameproof effect.

EXAMPLE XI

The needle felt described in the previous Example was treated with an aqueous impregnation solution having the following composition:

320 g/l of a reaction product of 1 mole of allyl alcohol, 2 moles of phospholane and 2 moles of ethylene oxide, 120 g/l of hexmethylol-melamine-pentamethylether, 6 g/l of ammonium chloride, 180 g/l of a 40% plastic dispersion, as has been described in Examples IX and X.

The squeezing-off effect on a two-roll padder was 105%. After a drying period of 28 minutes at 120° C the needle felt thus treated showed a flexible feel as well as a good retention of shape. The very good flameproof effect lasted for several wet treatments.

The same good flameproof effects — also with respect to permanence — were obtained, if instead of the above reaction product of 1 mole of allyl alcohol, 2 moles of phospholane and 2 moles of ethylene oxide, use was made of a reaction product having the following composition:

1 Mole of methanol, 2.5 moles of phospholane and 2.5 moles of ethylene oxide. The composition of the other components remained unaltered.

EXAMPLE XII

The needle felt floor covering described in Example I was treated on a two-roll padder with the following finishing bath:

280 g/l of a reaction product of 1 mole of ethylenediamine, 7.14 moles of phospholane and 8.6 moles of ethylene oxide, 160 g/l of trimethylol-melamine-trimethylether 210 g/l of a 40% plastic dispersion of ethylacrylate/acryonitrile/N-methylolacrylamide in the ratio of 6:3:1, 35 g/l of a 40% 2-amino-2-methyl-propanol-hydrochloride solution.

The squeezing-off effect was 97%. The drying was carried out for 25 minutes at 145° C. The needle felt was flexible and showed a good retention of shape. The flameproof effect was very good and lasted for several shampooings and washings.

The same good effects were obtained, when instead of the above-described reaction products, use was made of the following reaction products:
1. 1 Mole of m-phenylene-diamine and 6 moles of phospholane and 6.76 moles of ethylene oxide.
2. 1 Mole of benzidine and 7.7 moles of phospholane and 8.02 moles of ethylene oxide.

The amounts used were 300 g/l each time.

EXAMPLE XIII

A needle felt floor covering which consisted of 50% of fine-threaded polyester fibers with 50% of staple fibers and which was used as flameproof insulating material for building protection was treated with an aqueous impregnation solution of the following composition:

370 g/l of a reaction product of 1 mole of polyglycol 600, 8 moles of phospholane and 8.9 moles of ethylene oxide,
160 g/l of trimethylol-melamine-trimethylether.
200 g/l of a 50% polyvinylacetate dispersion,
5 g/l of ammonium chloride.

After the treatment on a two-roll padder with a squeezing-off effect of about 105% the material was dried for 25 minutes at 145° C and hardened. The flameproof effect was excellent.

EXAMPLE XIV

A needle felt floor covering, such as has been described in Example I, was treated on a two-roll padder with a finishing bath having the following composition:

250 g/l of a reaction product of 1 mole of 1,2-ethane-bis-methylphosphinic acid, 4 moles of phospholane, 6.3 moles of ethylene oxide,
230 g/l of a 50% hexamethylol-melamine-pentamethylether solution,
200 g/l of a 40% plastic dispersion of ethylacrylate/acrylonitrile/N-methylolacrylamide copolymer in the ratio of 6:3:1,
25 g/l of a 40% 2-amino-2-methyl-propanol-hydrochloride solution.

The squeezing-off effect was about 98%. The drying and condensation were carried out for 28 minutes at 145° C.

The needle felt thus finished did not show any hardening of the feel. It was filled, but flexible and had a good retention of shape. The flameproof effect was excellent and lasted for several wet treatments (shampooings and fine washings).

EXAMPLE XV

The needle felt described in Example I was treated with the same finishing bath which has also been mentioned in Example I. Instead of the 40% plastic dispersion of ethylacrylate/acrylonitrile/N-methylacrylamide 6:3:1 described, use was made of 160 g/l of an about 45% styrene/butylacrylate/acrylonitrile/methacrylic acid copolymer dispersion (ratio of 16:61:25:2:1).

A good permanent flameproof effect was also obtained, and the feel was full and flexible. The needle felt also showed a good retention of shape.

EXAMPLE XVI

A tufted carpet material having a weight per square meter of 600 g/m² and consisting of a polyamide loop pile of a height of 6 mm, which was tufted on a carrier material of needled polypropylene fleece, was provided with a pre-coating of the following composition:

300 Parts of a reaction product of 1 mole of glycol, 4 moles of 2,5-dioxo-2-methyl-1,2-oxa-phospholane and 4.3 moles of ethylene oxide or ethylene carbonate,
120 parts of a 80% trimethylol-melamine-trimethylether solution,
500 parts of a 3.5% methyl-hydroxyethyl-cellulose solution,
150 parts of a 50% butadiene-styrene dispersion (60:40),
75 parts of water,
5 parts of ammonium chloride,
600 parts of chalk.

The pre-coating was applied by means fo a rubber squeeze and was dried for 10 minutes at 140° C. The dry coating amount had a weight of about 800 g/m².

The tufted carpet thus treated showed a flexible feel, and the impregnative solution had not penetrated into the pile threads. The pile still showed its original looseness. The pile threads were excellently attached to the basic fabric.

Subsequently a carpet back coating was also applied with a rubber squeeze by way of a foaming process. The coating bath consisted of 205 parts of 50% butadiene-styrene dispersion (40/60),
14 parts of a paste containing vulcanization accelerators,
300 parts of chalk,
8 parts of a foaming agent on the basis of alkyl-naphthalenesulfonic acid-sodium salt.

The foaming was carried out in a ratio of 1:3 to the original volume. Following the doctor coating, the material was then dried for 10 minutes at 150° C. A smooth foam back was obtained which had a weight of about 900 g per square meter of dry coating. In a parallel test, a section of the above-described tufted material was provided with a pre-coating which did not contain any flameproof components. The bond coating was again effected by means of a 50% butadiene-styrene dispersion (60:40), chalk and methyl-hydroxyethyl cellulose as thickening agent. After drying, the above-described smooth foam was applied.

When the two carpet sections were tested according to DIN standard No. 54 332 following a flaming period of 15, 30 and 60 seconds, the tufted carpet which had not been finished with the flameproofing agent burned down all the way, whereas the carpet with a flameproof finish did not show any further burning or after-burn effect following the removal of the test flame.

According to the Nordtest method No. 7 for floor coverings, the following results were found: The carpet section which did not obtain any flameproof substance in the pre-coating, did not show any flameproof effect according to the Nordtest method No. 7. After the stack of wood had been extinguished, the carpet section continued to burn in a wide front over the measuring mark of 60 cm. The carpet section with a flameproof finish was extinguished immediately after the extinguishing of the stack of wood and showed a burning length of 28 cm, a burning width of 14 cm and an after-burn effect of 30 seconds. The smooth foam back which had not been provided with a flameproof finish was not affected by the flaming. This excellent flameproof effect was still maintained after five shampooings or after several wet treatments.

EXAMPLE XVII

The tufted carpet described in Example XVI was coated with a pre-coating composition which contained the following components:

320 Parts of a reaction product of 1 mole of glycerol, 6 moles of ethylene oxide or ethylene carbonate,
125 parts of a 80% trimethylol-melamine-trimethylether solution,
550 parts of a 3.5% methyl-hydroxyethyl-cellulose solution,
150 parts of a 50% butadiene-styrene dispersion (60:40),
50 parts of water,
5 parts of ammonium chloride,
400 parts of chalk.

The pre-coating was applied by means of a hand-operated doctor blade and was dried for 15 minutes at 135° C. The dry coating amount had a weight of about 870 g/m².

The tufted carpet thus treated showed a flexible feel after the treatment. The carpet pile was not adversely affected by the treatment, as the pre-coating composition did not penetrate the basic fabric. Subsequently a tufted back coating was applied by way of the foaming process. The coating bath consisted of:

250 Parts of a 50% butadiene-styrene dispersion (40:60),
16 parts of a paste containing vulcanization accelerators,
275 parts of chalk,
10 parts of a foaming agent on the basis of alkyl-naphthalenesulfonic acid-sodium salt.

The foaming was carried out in a ratio of 1:3. Following the coating with a hand-operated doctor, the material was dried for 15 minutes at 145° C. The dry coating amount of the smooth foam back had a weight of 870 g per square meter.

The tufted carpet thus treated did not continue to burn after the stack of wood had been extinguished, according to Nordtest method No. 7 for floor coverings. The burning length was 32 cm and the burning width 15 cm. After two minutes, there was no sign of an after-burn.

The smooth foam of the carpet back remained unaffected and did not show any damage by burning.

The flameproof effect had an excellent fastness to shampooing and lasted for several wet treatments.

EXAMPLE XVIII

A tufted carpet having a weight per square meter of 700 g consisted of a pre-needled polypropylene fleece and a polyester pile which had a blue color shade and a pile height of 5 mm. It was treated with a pre-coating composition which contained the following products:

250 Parts of a reaction product of 1 mole of glycol, 4 moles of 2,5-dioxo-2-methyl-1,2-oxa-phospholane and 4.3 moles of ethylene oxide or ethylene carbonate,
90 parts of a 80% trimethylol-melamine-trimethylether solution,
500 parts of a 3.5% methyl-hydroxy-cellulose solution,
170 parts of a 50 % butadiene-styrene dispersion (60:40),
70 parts of water,
5 parts of zinc chloride,
400 parts of zinc chloride,
400 parts of chalk.

The pre-coating was again applied by means of a hand-operated doctor blade and was dried for 12 minutes at 150° C. The weight of the dry coating was 900 g/m².

Subsequently a smooth foam was again applied onto the carpet back, as has been described in Examples 1 and 2.

In a parallel test a pre-coating without the flameproofing components, but with the same butadiene-styrene dispersion, was applied onto the same material, and afterwards the carpet back coating was carried out in accordance with Examples XVI and XVII by way of the foaming process.

According to the DIN test method No. 54 332 comprising a flaming period of 15, 30 and 60 seconds, the carpet test sample did not continue to burn after removal of the test flame. The tufted carpet sample which had not been provided with a flameproofing finish did continue to burn after removal of the test flame. The flameproof effect lasted for several shampooings.

EXAMPLE XIX

The tufted carpet described in Example XVIII was treated with a pre-coating composition which contained the following components:

300 Parts of a reaction product of 1 mole of glycol, 4 moles of 2,5-dioxo-2-methyl-1,2-oxa-phospholane and 4.3 moles of ethylene oxide or ethylene carbonate,
120 parts of a 80 % trimethylolamine-trimethylether solution,
500 parts of a 3.5 % methyl-hydroxyethyl-cellulose solution,
200 parts of a 40% plastic dispersion of ethyleneacrylate/acrylonitrile/N-methylolacrylamide copolymer in a ratio of 6:3:1,
75 parts of water,
20 parts of magnesium chloride,
3 parts of citric acid,
400 parts of chalk.

The pre-coating was applied by means of a rubber squeeze and was pre-heated on a stenter frame (10 sections) at 110° C; then it was hardened via a cylinder dryer for 5 minutes at 135° C. The wet coating on the rubber squeeze had a weight of 1300 g/m² and the dry coating had a weight of about 790 g/m².

Subsequently, a butadiene-styrene back coating was applied by way of the foaming process, as has been described in Example 1. According to the Nordtest method No. 7 for floor coverings, a burning length of 32 cm and a burning width of 16 cm were found; the flameproof effect was indeed excellent, since besides there was only an after-burn of 30 seconds.

The carpet section which did not contain any flameproof substance in the pre-coating and whose bond coating of the pile was effected only by way of the 40% plastic dispersion of ethylacrylate/acrylonitrile/N-methylolacrylamide with the addition of the thickening agent methyl-hydroxy-ethyl cellulose and chalk, burned in the flameproofing test according to the Nordtest method No. 7 beyond the 60 cm mark. In this process the carpet back coating was completely destroyed.

The flameproof finish lasted for eight shampooings and five wet treatments. Since the flameproof effect was still present to its full extent, the cleaning processes were discontinued.

EXAMPLE XX

A tufted carpet having a weight of 750 g/m² consisted of a pre-needled polypropylene fleece and a pile which had a brown color shade and a pile height of 6 mm and consisted of 80% of polyacylonitrile and 20% of polyamide threads.

Said tufted material was given a flameproof finish, as has been described in Example XVI.

According to Nordtest method No. 7 for floor coverings, a burning length of 45 cm and a burning width of 18 cm was found. The floor covering which had not been finished with a flameproof agent burned very rapidly beyond the 60 cm mark.

EXAMPLE XXI

A tufted carpet, as has been described in Example XVI, was treated with a pre-coating having the following composition:

280 Parts of a reaction product of 1 mole of pentaerythritol, 8 moles of 2,5-dioxo-2-methyl-1,2-oxa-phospholane and 8.4 moles of ethylene oxide or ethylene carbonate, 120 parts of a dimethylolurea-dimethylester solution of 80% strength, 500 parts of a 3.5% methyl-hydroxyethyl-cellulose solution, 170 parts of a 50% butadiene-styrene dispersion (60:40), 60 parts of water, 5 parts of ammonium chloride, 400 parts of chalk.

The pre-coating was effected according to the method described in Example XVII. Subsequently the material was dried for 20 minutes at 140° C in the drying cabinet. The dry coating had a weight of 870 g/m².

The further treatment was again carried out, as has been described in Example XVI. After a foam back of synthetic latex had been applied, a pre-gelatinizing was effected, then a honeycomb back was embossed on the synthetic latex coating by means of an embossing bowl, and the material was vulcanized for 10 minutes at 150° C. The tufted carpet thus treated and finished with a flameproof agent showed a highly elastic feel and met the requirements of Nordtest method No. 7 for floor coverings.

The burning length was 32 cm, the burning width 12 cm. After the stack of wood had been extinguished, the test sample did not continue to burn, only at two places an after-burn effect of 1 minute could be observed.

The flameproof effects were fast to shampooing.

EXAMPLE XXII

A tufted carpet, as has been described in Example XVIII, was provided with a pre-coating consisting of 230 parts of a reaction product of 1 mole of sorbitol, 12 moles of 2,5-dioxo-2-methyl-1,2-oxa-phospholane and 13.2 moles of ethylene oxide or ethylene carbonate, 95 parts of a 80% trimethylol-melamine-trimethylether solution, 450 parts of a 3.3% methyl-hydroxyethyl-cellulose solution, 180 parts of a 50% butadiene-styrene dispersion (60:40), 70 parts of water, 5 parts of zinc chloride, 410 parts of chalk.

The application and further treatment was effected, as has been described in Example XVIII.

A tufted carpet was obtained which had very good flameproof properties.

EXAMPLE XXIII

A printed polyamide woven carpet having a weight per square meter of 800 g and a pile height of 5 mm was provided with a carpet back coating. As feel-improving component, a 50% polyvinylacetate dispersion was used, and a methyl-hydroxyethyl-cellulose solution as thickening agent.

A woven carpet thus finished burned down under the action of flames, however.

Said carpet was therefore provided with a carpet back finish which had the following composition:

300 Parts of a reaction product of 1 mole of glycol, 4 moles of 2,5-dioxo-2 -methyl-1,2-oxa-phospholane and 4.3 moles of ethylene oxide or ethylene carbonate, 120 parts of a 80% trimethylol-melamine-trimethylether solution, 500 parts of a 3.5% methyl-hydroxyethyl-cellulose solution, 200 parts of a 50% polyvinylacetate dispersion, 50 parts of water, 5 parts of ammonium chloride.

The pre-coating was applied by means of a rubber squeeze and was dried for 10 minutes at 135° C. The dry coating had a weight of about 450 g/m². The flameproof carpet back finish was flexible. According to DIN No. 54 332, the carpet showed after a flaming period of 15, 30 and 60 seconds an excellent flameproof effect. After removal of the test flame, the carpet did not continue to burn.

What is claimed is:

1. Compounds of the general formula

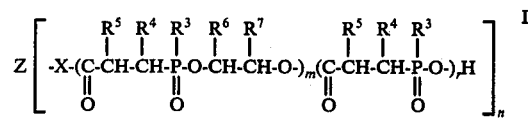

in which

X is oxygen $R^3$ is a $(C_1-C_4)$-alkyl group which may be substituted, preferably monosubstituted, by halogen, especially chlorine, a cylcoalkyl group having up to 8 carbon atoms, especially cyclopentyl, cyclohexyl, an alkenyl group having up to 4 carbon atoms, especially vinyl and allyl, a phenyl or benzyl group optionally substituted by halogen, preferably chlorine and/or bromine, and preferably carrying 1 to 3 substituents, $R^4$ is hydrogen or a $(C_1-C_4)$-alkyl group, preferably methyl, $R^5$ is hydrogen or a $(C_1-C_2)$-alkyl group, preferably methyl, with at least one of the radicals $R^4$ and $R^5$ preferably being hydrogen, $R^6$ is hydrogen, methyl, chloromethyl, $R^7$ is hydrogen, methyl or ethyl, preferably hydrogen, $m$ stands for numbers in the range of from 1 to 20, preferably from 2 to 20, especially 20 to 6, $n$ stands for numbers in the range of from 1 to 6, preferably from 2 to 6, $r$ is 0 or 1, preferably 0, Z is a $n$-valent radical of the group consisting of: straight-chain or branched hydrocarbon radicals having from 1 to 18, preferably from 1 to 12, carbon atoms which may be interrupted by up to 8 —O-atoms, generally up to (q/2 − 1) —O-atoms, if q is the number of carbon atoms in Z, and/or by up to 3 —S-atoms and/or NR² radicals with R² being (C₁-C₄)-alkyl, especially methyl, and/or may be substituted by fluorine, chlorine, bromine atoms, preferably Cl and Br, while carrying preferably substituents in a number of up to half the H-atoms contained in Z, especially from 1 to 4; cyclohexyl radicals which may be substituted by from 1 to 3, preferably one straight-chain or branched and/or unsaturated alkyl radical having from 1 to 4 carbon atoms, or by a (C₁-C₄)-alkyl radical carrying preferably up to 4 F, Cl, or Br-atoms; aromatic or araliphatic radicals which are derived from benzene, alkyl benzenes having up to 18 carbon atoms, from naphthalene, diphenyl, diphenylmethane, diphenylethane or 2,2-diphenylpropane, and which may be substituted in the nucleus by 1 or 2 methoxy and/or ethoxy groups, and which may be substituted in the nucleus and/or the lateral chains by F, Cl or Br-atoms, preferably carrying up to 5 substituents, or phosphate-containing radicals of the general formula

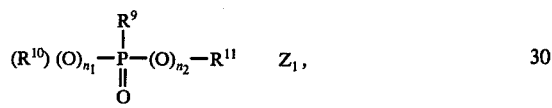

in which
$n_1$, $n_2$ are independently from each other 0 and 1 and R⁹ stands for alkyl, hydroxyalkyl, optionally (C₁-C₂)-alkylated and/or -dialkylated aminoalkyl, halogeno- (preferably choloro-)alkyl having 1 to 3 carbon atoms, alkenyl having 2 or 3 carbon atoms or phenyl optionally substituted by 1 or 2 halogen atoms, preferably Cl or Br,
R¹⁰, R¹¹ may be defined as R⁹ — if the pertinent $n_1$ and/or $n_2$ equals 0 — with the restriction that for $n_1=n_2=0$ at least one of the radicals R¹⁰, R¹¹ is an (C₁-C₃)-alkylene radical or, if the pertinent $n_1$ and/or $n_2$ equals 1, is a straight-chain or branched alkylene radical having from 2 to 5 carbon atoms or is the radical

or represent phosphorous-containing radicals of the general formula

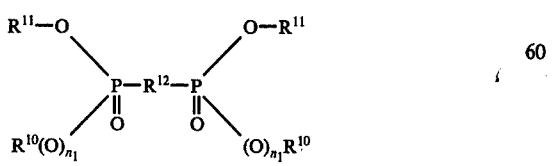

with $n_1$, R¹⁶, R¹¹ being defined as in Z₁ and R¹² being a straight-chain or branched (C₁-C₆)-alkylene, phenylene, xylylene radical or a radical

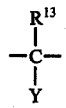

with Y = OH, NH₂ and R¹³ = (C₁-C₃)-alkyl, or phosphorus-containing radicals of the general formula

in which R⁴, R⁵, R⁶, R⁷ are defined as in formula I above and R¹⁴ is defined as R³ or represents the group —O—CHR⁶—CHR⁷.

2. Compounds of the formula I as claimed in claim 1, in which Z is alkyl with 2 to 6 carbon atoms, X is oxygen, n and m represent integers of 2 to 6, r equals 0, R⁴ to R⁷ stand for hydrogen or methyl, and R³ is methyl, ethyl or phenyl.

3. Process for the preparation of compounds of formula I, which comprises mixing a compound of the formula $$Z(\text{—X—H})_n \qquad\qquad \text{II}$$

(a₁) with the about n times molar amount of a phospholane of the formula

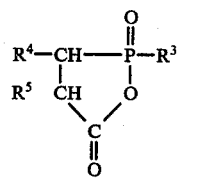

heating it at a temperature of from 0° to 180° C, preferably 80° to 150° C, to give a phosphinic acid of the formula

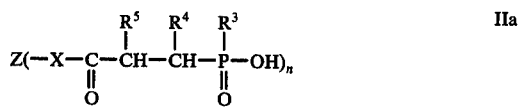

and, when this reaction has been completed, which can be seen from the disappearing of the phospholane peak at 5 500 mµ, (a₂) mixing the product thus obtained with the about n times molar amount of an alkylene oxide of the formula

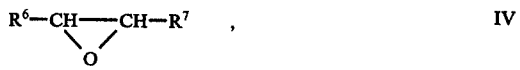

reacting it at a temperature of from 80° to 180° C, preferably from 100° to 150° C, to give a phosphinic acid(hydroxyalkyl)-ester of the formula

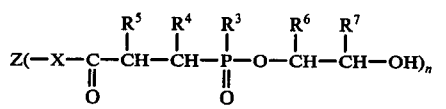

and, when this reaction has been completed, which can be seen from the acid number being 0 at the above reaction temperatures, i.e. from 80° to 180° C, preferably from 100° to 150° C, repeating the operation $a_1 (m-1+r)$ times and following every operation $a_1$, repeating the operation $a_2 - (m-1)$ times altogether —, or, preferably, (b$_1$) mixing a compound of the formula II with the about $n(m+r)$ times molar amount of a phospholane of the formula III at a temperature of from 80° to 180° C, preferably from 100° to 150° C and, after the reaction heat has cooled off, (b$_2$) mixing the product with the about $n \cdot m$ times molar amount of an alkylene oxide of the formula IV and further maintaining the mixture, preferably while stirring, at the reaction temperature, until the reaction has been completed, which can be seen from the disappearing of the phospholane peak and/or when $r$ equals 0, also of the acid number.

4. Process as claimed in claim 3, which comprises mixing the phosphinic acid of the formula IIa (a$_2$) with the about $n$ times molar amount of an alkylene carbonate of the formula

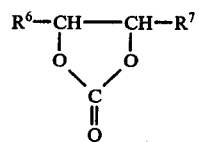

reacting it at a temperature of from 130° to 250° C, preferably from 160° to 220° C, to give a phosphinic acid(hydroxyalkyl)-ester of the formula

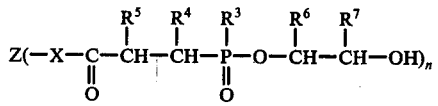

and after the reaction has been completed, which can be seen from the disappearing of the acid number at the above-mentioned reaction temperatures, repeating the operation $a_1$ $(m-1+r)$ times and following every operation $a_1$, repeating the operation $a_2 - (m-1)$ times altogether—, or, preferably, (b$_1$) mixing a compound of the formula II with the $n \cdot m$ times molar amount of a phospholane of the formula III at a temperature of form 10° to 180° C, preferably from 20° to 120° C, and after the reaction heat has cooled off, (b$_2$) mixing the product with the about $n \cdot m$ times molar amount of an alkylene oxide of the formula IV and further maintaining the mixture, preferably while stirring, at the reaction temperature, until the reaction has been completed, which can be seen from the disappearing of the carbon dioxide development and/or for $r = 0$, also of the acid number.

* * * * *